US010506944B2

(12) United States Patent
Tognetti et al.

(10) Patent No.: US 10,506,944 B2
(45) Date of Patent: Dec. 17, 2019

(54) APPARATUS FOR ELECTRODERMAL ACTIVITY MEASUREMENT WITH CURRENT COMPENSATION

(71) Applicant: Empatica Srl, Milan (IT)

(72) Inventors: Simone Tognetti, Vimodrone (IT); Ivan Cenci, Verucchio (IT); Daniele Resnati, Carate Brianza (IT); Maurizio Garbarino, Turin (IT); Matteo Lai, San Sperate (IT)

(73) Assignee: Empatica Srl, Milan (IT)

( * ) Notice: Subject to any disclaimer, the term of this patent is extended or adjusted under 35 U.S.C. 154(b) by 365 days.

(21) Appl. No.: 14/215,613

(22) Filed: Mar. 17, 2014

(65) Prior Publication Data

US 2014/0316229 A1    Oct. 23, 2014

Related U.S. Application Data

(60) Provisional application No. 61/802,500, filed on Mar. 16, 2013, provisional application No. 61/802,519, filed on Mar. 16, 2013.

(51) Int. Cl.
*A61B 5/053* (2006.01)
*A61B 5/0205* (2006.01)
(Continued)

(52) U.S. Cl.
CPC ............ *A61B 5/053* (2013.01); *A61B 5/0205* (2013.01); *A61B 5/0531* (2013.01);
(Continued)

(58) Field of Classification Search
None
See application file for complete search history.

(56) References Cited

U.S. PATENT DOCUMENTS 3,556,083 A   1/1971  Grichnik et al.
3,784,908 A   1/1974  Anderson
(Continued)

FOREIGN PATENT DOCUMENTS

CN    2610843 Y    4/2004
CN    1985701 A    6/2007
(Continued)

OTHER PUBLICATIONS

International Search Report and Written Opinion for International Application No. PCT/EP2014/055304, dated Jun. 5, 2014, 13 pages.
(Continued)

*Primary Examiner* — Matthew Kremer
(74) *Attorney, Agent, or Firm* — Cooley LLP

(57) ABSTRACT

An apparatus for measuring electrodermal activity can include a first electrode in contact with a first portion and a second electrode in contact with a second portion of a stratum corneum, and in electronic communication with the second electrode through the stratum corneum. A processing module is electrically coupled to the first electrode and the second electrode and is operable to (a) bias the first electrode at a first voltage V+ and the second electrode at a second voltage V− (b) measure a current flowing between the first electrode and the second electrode, the current corresponding to the conductance of the stratum corneum, (c) subtract a compensation current from the measured current (d) measure a resulting current producing an amplified output voltage (e) measure a conductance of the stratum corneum, and (f) adjust at least one of the first voltage, the second voltage and the compensation current to desaturate the output voltage.

19 Claims, 16 Drawing Sheets

(51) Int. Cl.
*A61B 5/00* (2006.01)
*A61B 5/024* (2006.01)

(52) U.S. Cl.
CPC ............ *A61B 5/0533* (2013.01); *A61B 5/681* (2013.01); *A61B 5/6802* (2013.01); *A61B 5/02405* (2013.01); *A61B 5/02438* (2013.01); *A61B 2562/0215* (2017.08); *A61B 2562/0219* (2013.01)

(56) References Cited

U.S. PATENT DOCUMENTS

| | | | | |
|---|---|---|---|---|
| 5,284,150 | A * | 2/1994 | Butterfield | A61B 5/021 600/485 |
| 2005/0039742 | A1* | 2/2005 | Hickle | A61B 5/02416 128/203.14 |
| 2007/0173803 | A1* | 7/2007 | Wham | A61B 5/053 606/34 |
| 2007/0213020 | A1* | 9/2007 | Novac | A61B 5/0245 455/139 |
| 2008/0208016 | A1* | 8/2008 | Hughes | A61B 5/0533 600/301 |
| 2008/0214903 | A1* | 9/2008 | Orbach | G06Q 50/22 600/301 |
| 2011/0092780 | A1* | 4/2011 | Zhang | A61B 5/053 600/301 |
| 2011/0093780 | A1 | 4/2011 | Dunn et al. | |
| 2012/0123291 | A1 | 5/2012 | Lin | |
| 2012/0296175 | A1* | 11/2012 | Poh | A61B 5/02405 600/301 |

FOREIGN PATENT DOCUMENTS

| | | |
|---|---|---|
| CN | 101198277 A | 6/2008 |
| EP | 2131731 B1 | 12/2009 |
| EP | 2 322 395 A1 | 5/2011 |
| JP | 2004-000655 A | 1/2004 |
| JP | 2006-068492 A | 3/2006 |
| WO | WO 2006/090371 A2 | 8/2006 |
| WO | WO 2008/099288 A2 | 8/2008 |
| WO | WO 2010/085969 A1 | 8/2010 |
| WO | WO 2012/140537 | 10/2012 |

OTHER PUBLICATIONS

Office Action dated Jul. 30, 2018 for Japanese Application No. 2015-562259, with English translation, 10 pages.
Office Action dated Jan. 19, 2018 for Chinese Application No. 201480025005.8, with English translation, 28 pages.
Office Action dated Jan. 29, 2018 for Japanese Application No. 2015-562259, with English translation, 10 pages.
Office Action dated Oct. 24, 2018 for Chinese Application No. 201480025005.8, with English translation, 11 pages.
Office Action dated May 21, 2019 for Chinese Application No. 201480025005.8, w/ English Translation, 9 pages.

* cited by examiner

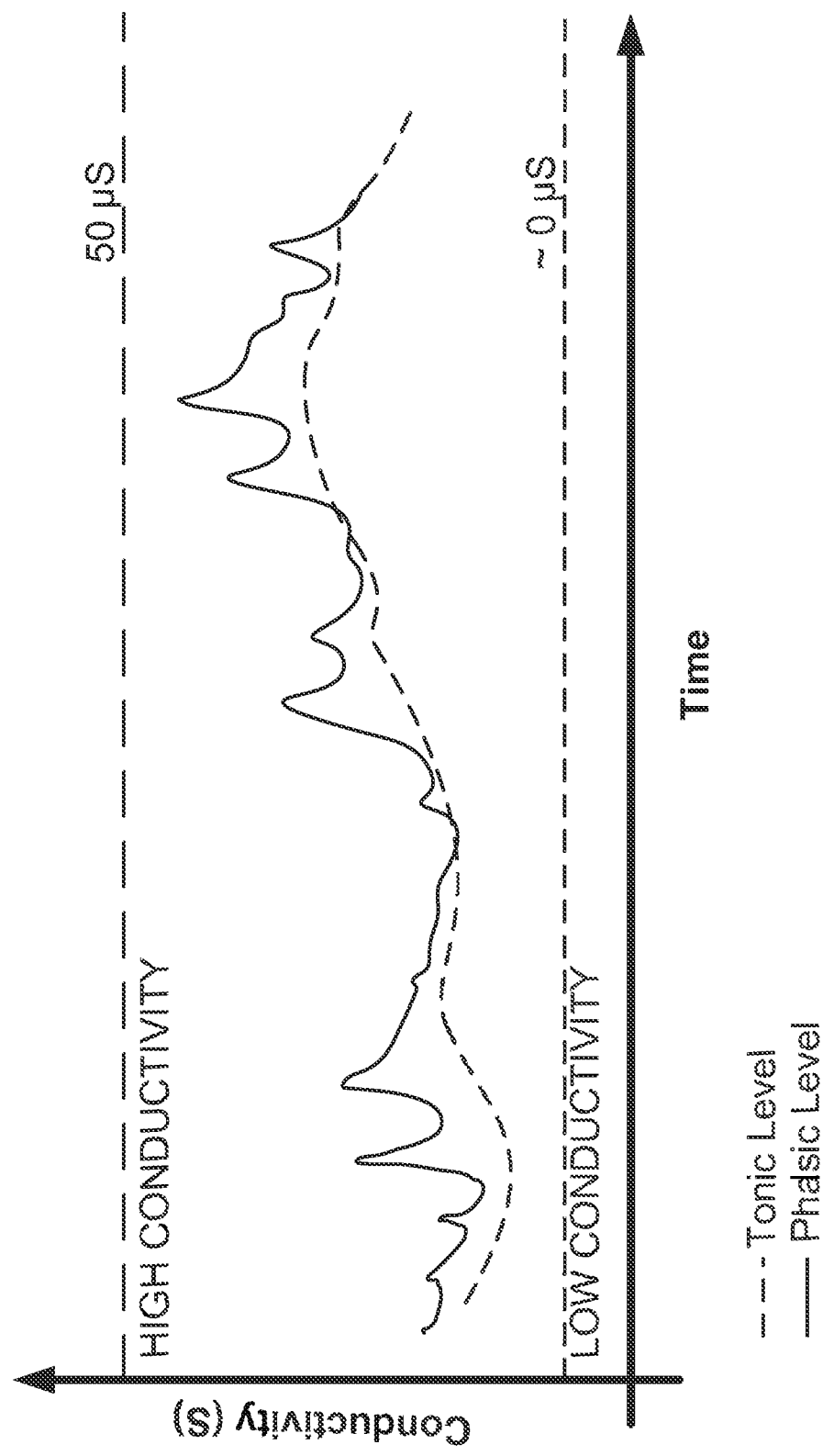

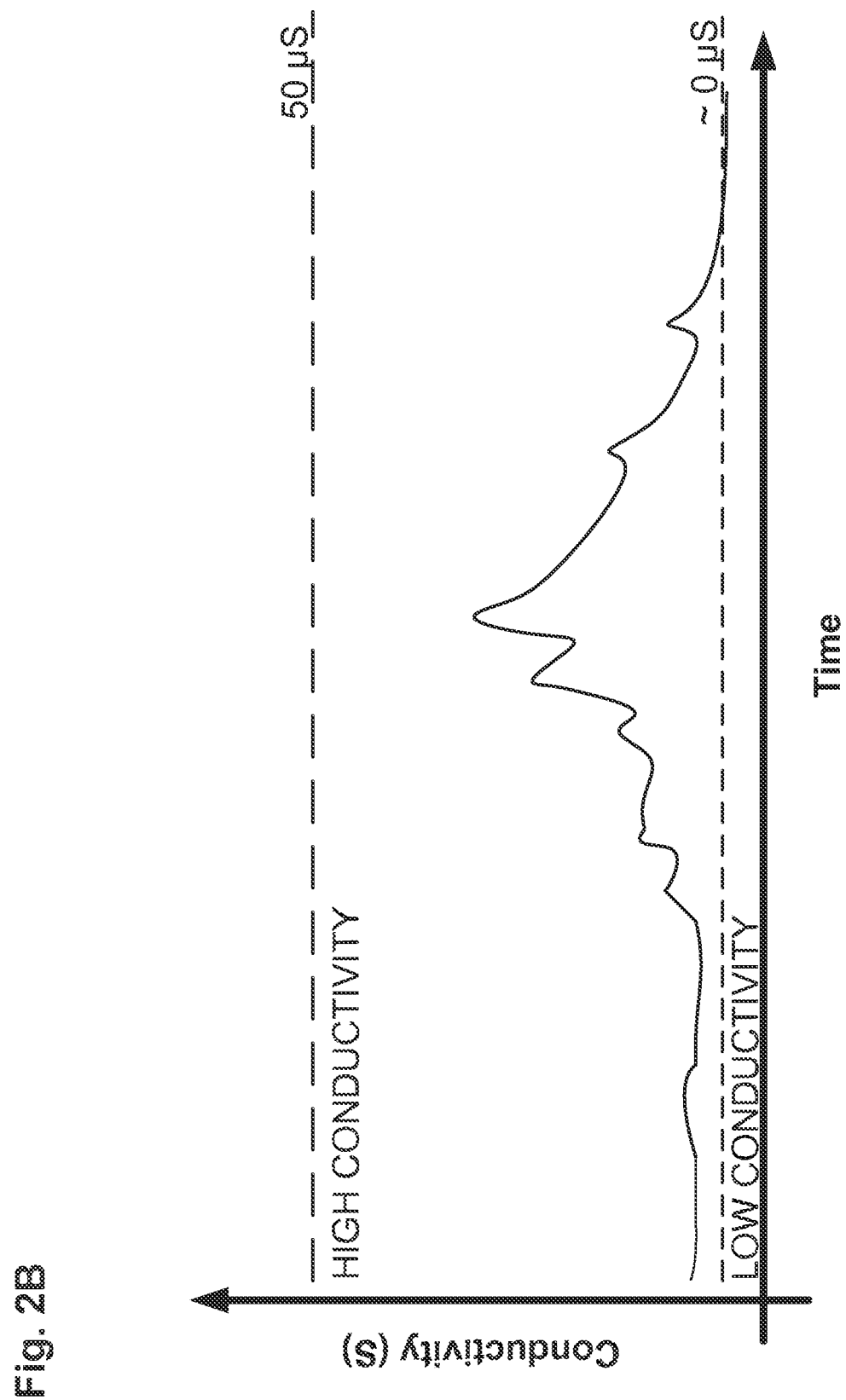

APPARATUS FOR ELECTRODERMAL ACTIVITY MEASUREMENT WITH CURRENT COMPENSATION

CROSS REFERENCE TO RELATED APPLICATIONS

This application claims priority to and benefit of U.S. Provisional Patent Application No. 61/802,500, entitled, "Apparatus for Electro Dermal Activity Measurement with Current Compensation," filed Mar. 16, 2013, and U.S. Provisional Patent Application No. 61/802,519, entitled "Method for Estimating Human Well-being Through Heart Rate Variability," filed Mar. 16, 2013, the disclosures of which are incorporated by reference herein in their entirety.

BACKGROUND

Embodiments described herein relate generally to devices, systems and methods for measuring electrodermal activity, and in particular to wearable devices and methods for measuring electrodermal activity of the skin of a user.

The human skin is composed of different layers of tissue. These layers of tissue perform several functions, for example, forming an interface between the internal and external parts of the body, serve as a protection mechanism, have a thermoregulatory function, and allow exchange of fluids through the skin. The human skin also includes sweat glands that produce sweat. The sweat includes various electrolytes which allow current to be conducted through the skin. For example, if two electrodes capable of producing free ions such as, for example, silver (Ag) electrodes are disposed on the skin, free ions can be electronically communicated between the two electrodes via the skin.

The conductance of skin, which is generally referred to as the electrodermal activity, is extremely low and is generally measured in Siemens (S). The conductance of the skin depends upon the thickness of the stratum corneum. The inner layer of the skin creates a potential barrier which changes in size and allows the current to flow in a less or more restricted way in the stratum corneum. The thinner the stratum corneum, the higher is the conductance. For example, the conductance of skin at the finger tips can be in the range of about 0.5 μS to about 50 μS, and the conductance of the skin at the wrist can be in the range of about 0.05 μS to about 80 μS. These variations can depend on many factors, including the physiology of an individual, temperature, skin structure, and autonomous nervous system (ANS) activity.

The electrodermal activity signal generally includes two interleaved signals; the tonic level and phasic level. The tonic level (also referred to herein as "tonic level conductance") is the skin conductance in the absence of any external or environmental stimuli, is slow changing (i.e., low frequency), and is caused by the human physiological factors as described herein. The tonic level can have a range of about 0.05 μS to about 50 μS at the wrist of a user.

The phasic level (also referred to herein as "phasic level conductance") is typically associated with short-term events and occurs in the presence of discrete environmental stimuli such as for example, sight, sound, smell, and cognitive processes that precede an event such as anticipation, decision making, etc. Phasic changes usually show up as abrupt increases in the skin conductance, or "peaks" in the skin conductance.

Systems and devices can also be used to measure heart rate variability (HRV) through the skin, or in the blood beneath the skin of the user. The HRV is defined as the beat-to-beat variations in heart rate. The larger the alterations, the larger the HRV. HRV is a known predictor of mortality of myocardial infarction and other pathological conditions may also be associated with modified (usually lower) HRV, including congestive heart failure, diabetic neuropathy, depression post-cardiac transplant, susceptibility to sudden infant death syndrome (SIDS), and poor survival in premature babies. HRV is also related to emotional arousal. HRV has been found to decrease during conditions of acute time pressure and emotional strain, elevated levels of anxiety, or in individuals reporting a greater frequency and duration of daily worry.

HRV includes two primary components: respiratory sinus arrhythmia (RSA) which is also referred to as high frequency (HF) oscillations, and low frequency (LF) oscillations. HF oscillations are associated with respiration and track the respiratory rate across a range of frequencies, and low frequency oscillations are associated with Mayer waves (Traube-Hering-Mayer waves) of blood pressure. The total energy contained by these spectral bands in combination with the way energy is allocated to them gives an indication of the heart rate regulation pattern given by the central nervous system, and an indication of the state of mental and physical health.

However, known methods for analyzing heart beat data to determine HRV and a psychophysical state of a person often fail to determine a true mental and physical state of the person. Some known HRV spectral analysis methods use non-parametric approaches (e.g., Fast Fourier transforms) or parametric approaches. These strategies rely on the approximation that the tachogram is "sampled" at a constant frequency. Such known methods are susceptible to missing beat data or high variability in the heart beat data. Furthermore, high activity can also lead to high variability in the heart beat data which cannot be analyzed properly by known methods.

Thus, there is a need for new systems, devices and methods that can measure skin conductance with high reliability, repeatability and do not suffer from electrolysis. Furthermore, there is also a need for new methods to analyze heart beat data and determine human well being through heart rate variability.

SUMMARY

Embodiments described herein relate generally to devices, systems and methods for measuring electrodermal activity, and in particular to wearable devices and methods for measuring electrodermal activity of the skin of a user. In some embodiments, an apparatus for measuring electrodermal activity can include a first electrode in contact with a first portion of stratum corneum of skin and a second electrode in contact with a second portion of stratum corneum. The first electrode can be in electronic communication with the second electrode through the stratum corneum. A processing module is electrically coupled to the first electrode and the second electrode. The processing module is operable to (a) bias the first electrode at a first voltage V+ and the second electrode at a second voltage V−, (b) measure a current flowing between the first electrode and the second electrode, the current corresponding to the conductance of the stratum corneum, (c) subtract a compensation current from the measured current, (d) measure a resulting current and produce an amplified output voltage, (e) measure a conductance of the stratum corneum, and (f) adjust at least one of the first voltage, the second voltage and the compensation current to desaturate the output voltage.

BRIEF DESCRIPTION OF THE DRAWINGS

FIG. 2A is a plot of an electrodermal activity signal measured on skin of that includes the tonic level conductance and the phasic level conductance.

FIG. 2B is a plot of a typical electrodermal activity signal ranging from low to high values.

DETAILED DESCRIPTION

Figure 1A:
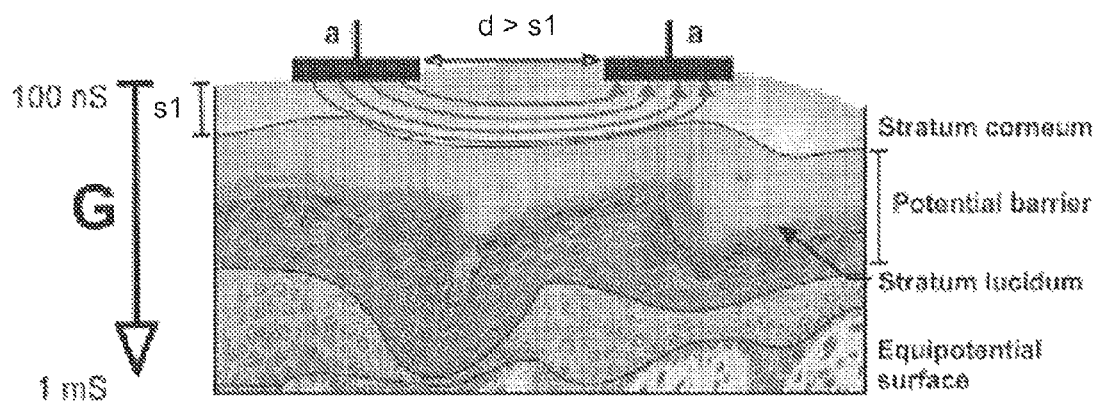
FIG. 1A is a cross-section of skin of a human with the stratum corneum of the skin at a first thickness and having a first conductance.

Embodiments described herein relate generally to devices, systems and methods for measuring electrodermal activity, and in particular to wearable devices and methods for measuring electrodermal activity of the skin of a user. Measurement of the two different frequency conductances that define the electrodermal activity of a human can be challenging. The tonic level has a wide range which can be difficult to encompass with conventional electrodermal activity monitors. Furthermore, the phasic level is fast changing and can be difficult to resolve with conventional electrodermal activity monitors.

Electrodes used for electrodermal sensing can also undergo electrolysis on the skin. As the current flows through the skin, the electrode (e.g., a Ag electrode) can lose metal ions which can get deposited on the skin. This can lead to corrosion of the electrode, and can also lead to skin irritation because of the metal ions.

Conventional electrodermal activity sensors can be DC current sensors or AC current sensors. DC current based electrodermal activity sensors generally give good performance in measuring both tonic level conductance and phasic level conductance but can suffer from electrolysis. In contrast, AC current based electrodermal activity sensors give good performance in measuring tonic level conductance and have little or no electrolysis but demonstrate poor performance in measuring phasic level conductance.

Embodiments of the systems, devices and methods described herein can provide a compensation mechanism for reliably measuring the tonic level and phasic levels of the conductance of the skin. The electrodermal activity measurement systems, devices and methods described herein provide several advantages over conventional electrodermal activity sensors including, for example: (1) capability of measuring electrodermal activity over a wide range that covers the entire range of expected tonic level conductances, (2) capability of measuring phasic level conductances with high resolution, (3) reduction in electrolysis of sensing electrodes, and (4) allowing real time electrodermal activity measurement by integration in a wearable device, for example, a wrist band.

In some embodiments, an apparatus for measuring electrodermal activity can include a first electrode in contact with a first portion of a stratum corneum of skin and a second electrode in contact with a second portion of the stratum corneum. The first electrode can be in electronic communication with the second electrode through the stratum corneum. A processing module is electrically coupled to the first electrode and the second electrode. The processing module is operable to (a) bias the first electrode at a first voltage V+ and the second electrode at a second voltage V−, (b) measure a current flowing between the first electrode and the second electrode, the current corresponding to the conductance of the stratum corneum, (c) subtract a compensation current from the measured current, (d) measure a resulting current and produce an amplified output voltage, (e) measure a conductance of the stratum corneum, and (f) adjust at least one of the first voltage, the second voltage and the compensation current to desaturate the output voltage.

In some embodiments, a wearable device for measuring electrodermal activity can include a housing configured to be removably associated with the skin of a user. A first electrode and a second electrode are included in the device such that at least a portion of the first electrode and the second electrode are disposed outside the housing. The first electrode is configured to contact a first portion of a stratum corneum of skin and the second electrode is configured to contact a second portion of the stratum corneum of the skin when the housing is associated with the user. A processing module is also disposed in the housing and coupled to the first electrode and the second electrode. The processing module is operable to (a) bias the first electrode at a first voltage V+ and the second electrode at a second voltage V−, (b) measure a current flowing between the first electrode and the second electrode, the current corresponding to the conductance of the stratum corneum, (c) subtract a compensation current from the measured current, (d) measure a resulting current and produce an amplified output voltage, (e) measure a conductance of the stratum corneum, and (f) adjust at least one of the first voltage, the second voltage and the compensation current to desaturate the output voltage. A communications module is also disposed in the housing and coupled to the processing module. The communications module can be configured to at least one of a display an electrodermal activity of the user and communicate electrodermal activity data from the processing module to an external device. A power source is also disposed in the housing and is configured to provide electrical power to the processing module and the communications module. In some embodiments, the wearable device can be a wrist band.

In some embodiments, a method for measuring electrodermal activity can include disposing a first electrode and a second electrode on a stratum corneum of a user. The first electrode is biased at a first voltage and the second electrode is biased at a second voltage. An output voltage proportional to the current flowing through the skin is measured. The method transforms the output voltage into a conductance level and determines if it is saturated or not. If the output voltage is saturated low, the compensation current is increased or the difference in voltage between the two electrodes is decreased to change the output voltage such that it is not saturated. If the output voltage is saturated high, the compensation current is decreased or the difference in voltage between the two electrodes is increased to change the output voltage such that it is not saturated. In some embodiments, the measured conductance is a tonic level conductance having a value in the range of about 0.05 µS to about 50 µS.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof As used herein, the terms "about" and "approximately" generally mean plus or minus 10% of the value stated. For example, about 0.5 would include 0.45 and 0.55, about 10 would include 9 to 11, about 1000 would include 900 to 1100.

Figure 1B:
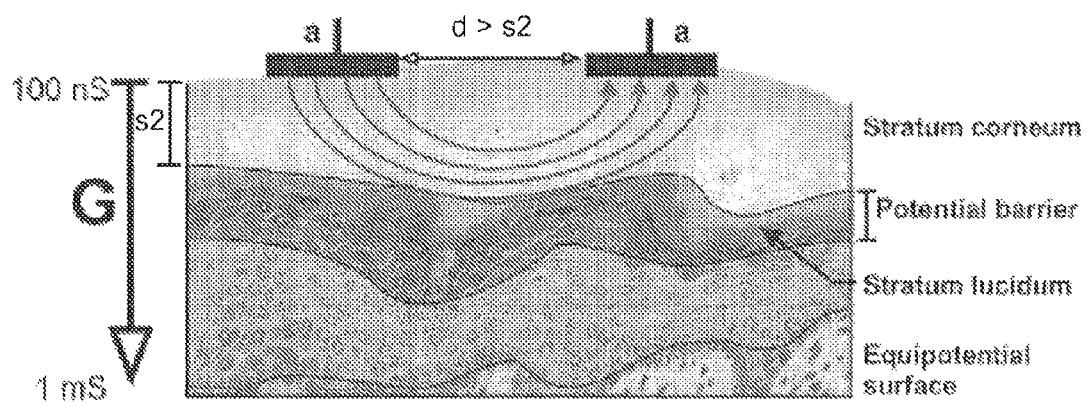
FIG. 1B is a cross-section of the skin showing the stratum corneum at a second thickness and having a second conductance.

The embodiments described herein can be used to measure the electrodermal activity (i.e., conductance including tonic level and phasic level conductance) of a stratum corneum of a skin. For reference, FIG. 1A shows a cross section of a skin of a human. The outermost layer of the skin is the stratum corneum. Below the stratum corneum is the stratum lucidum. A potential barrier exists between the stratum corneum and the stratum lucidum. The conductance of the skin varies, as shown by the arrow G from about 100 nS at a top surface of the stratum corneum to about 1 mS near a bottom surface of the skin which is a substantially equally potential surface. As shown in FIG. 1A, the stratum corneum can have a first thickness s1 measured from a top surface of the stratum corneum to the potential barrier. When a pair of electrodes "a-a" are placed in electronic communication with the stratum corneum such that the distance between the electrodes is greater than the first thickness s1 of the stratum corneum the stratum corneum can have a first conductance. The various factors affecting the conductance of the skin, for example, the physiology of an individual, temperature, skin structure, and autonomous nervous system (ANS) activity, do so by changing the thickness of the stratum corneum. The stratum corneum serves essentially as a potential barrier that changes in size and thickness. As shown in FIG. 1B, the thickness of the stratum corneum can increase to a second thickness s2 substantially greater than s1. Change in thickness also changes the conductance of the stratum corneum. The thinner the stratum corneum, the higher the conductance. Thus, the pair of electrodes a-a when placed in electronic communication with the stratum corneum such that the distance between the electrodes a-a is greater than the second thickness s2 of the stratum corneum, will measure a second conductance less than the first conductance. Thus, changes in conductance of the stratum corneum can be directly correlated to the physiological status of a user, for example, the ANS activity.

FIG. 2A shows an exemplary electrodermal activity measurement showing changes in the tonic level and phasic level conductances of a human. The tonic level can be characterized as "a smooth underlying slowly-changing conductance level." The phasic level conductance can be characterized as "rapidly changing peaks." Tonic level conductance level can slowly vary over time in an individual depending upon his or her psychological state, hydration, skin dryness, and autonomic regulation. Tonic changes in the skin conductance level typically occur in a period from tens of seconds to minutes. Phasic level conductance measurements are typically associated with short-term events and occur in the presence of discrete environmental stimuli (sight, sound, smell, cognitive processes that precede an event such as anticipation, decision making, etc). Phasic changes usually show up as abrupt increases in the skin conductance, or "peaks" in the skin conductance. FIG. 2B shows a typical electrodermal activity signal ranging from low to high values.

Figure 3:
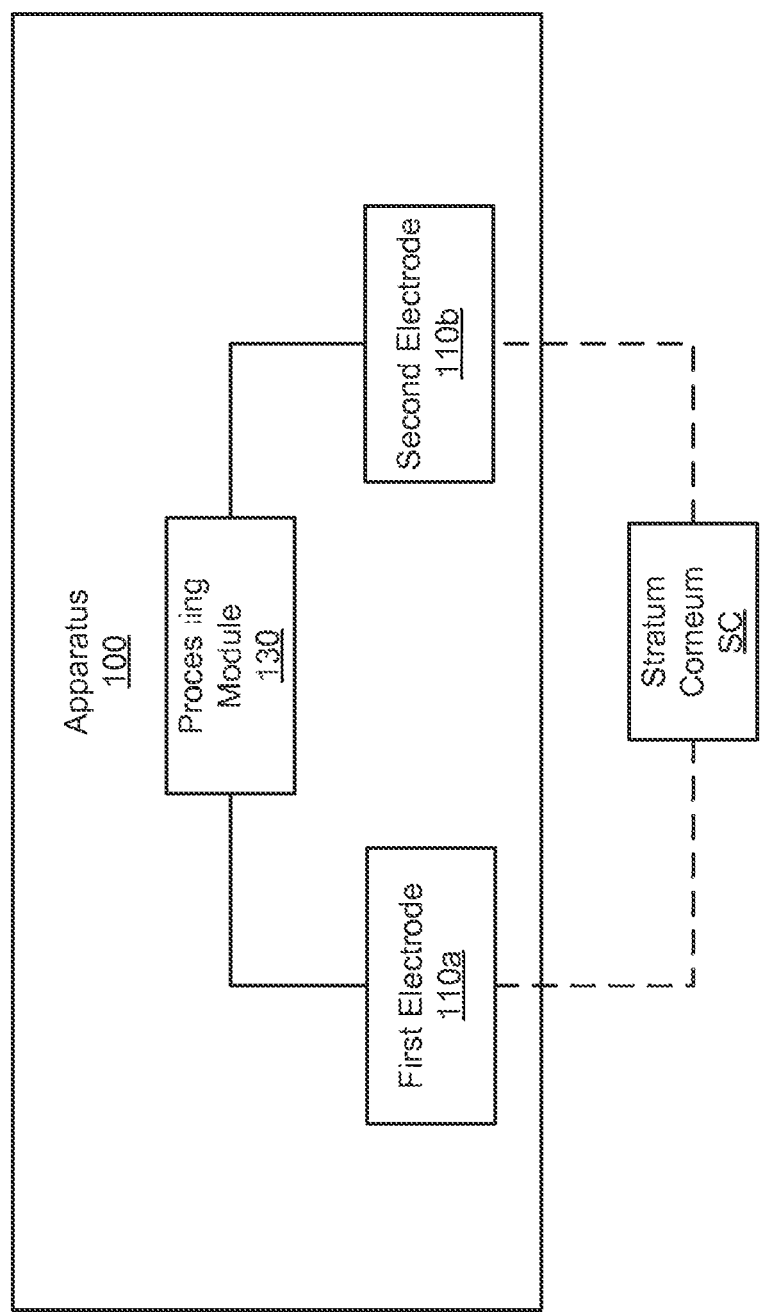
FIG. 3 shows a schematic block diagram of an apparatus for measuring electrodermal activity, according to an embodiment.
Figure 4:
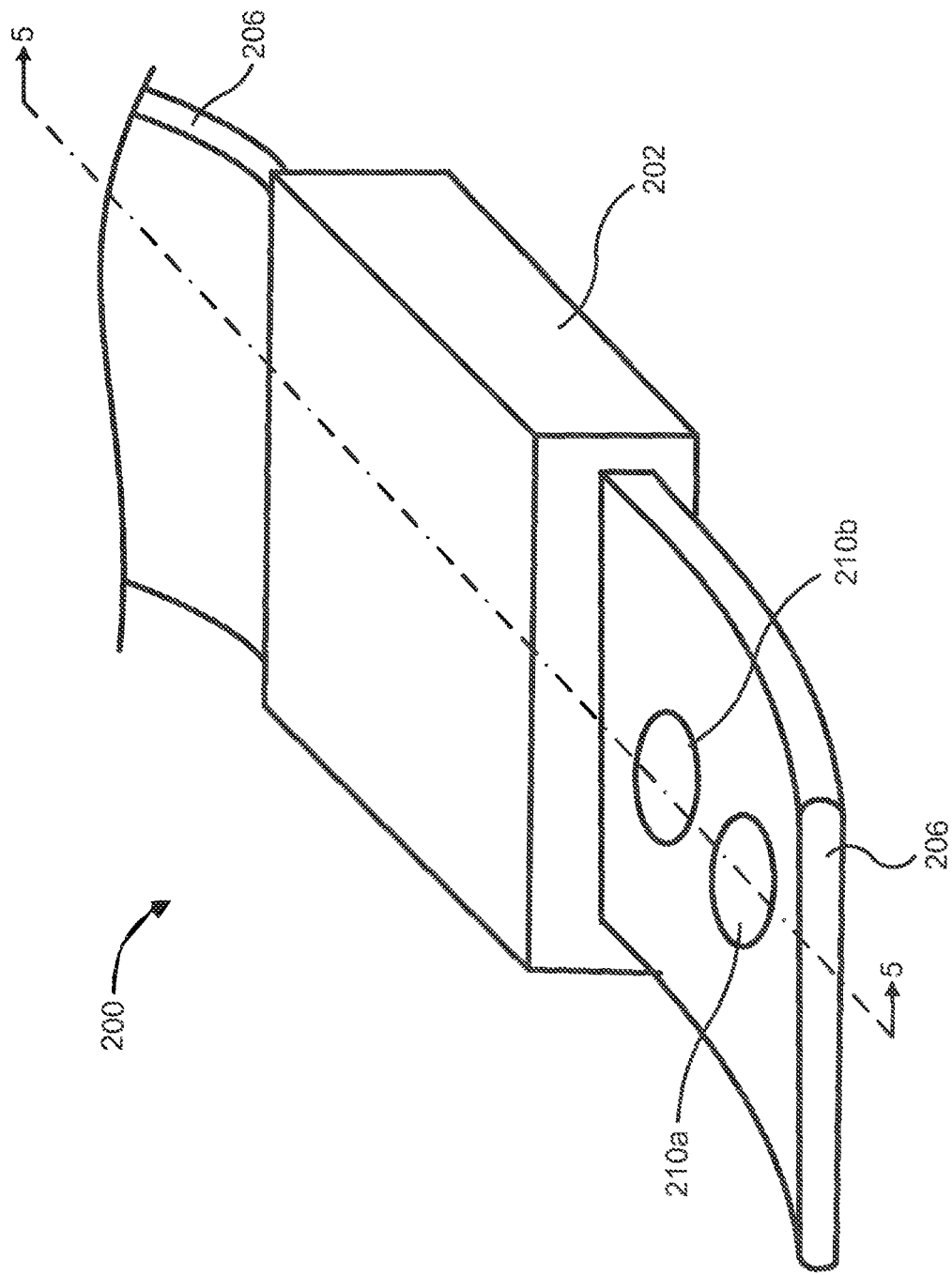
FIG. 4 shows a bottom perspective view of a wearable device for measuring electrodermal activity, according to an embodiment.
Figure 5:
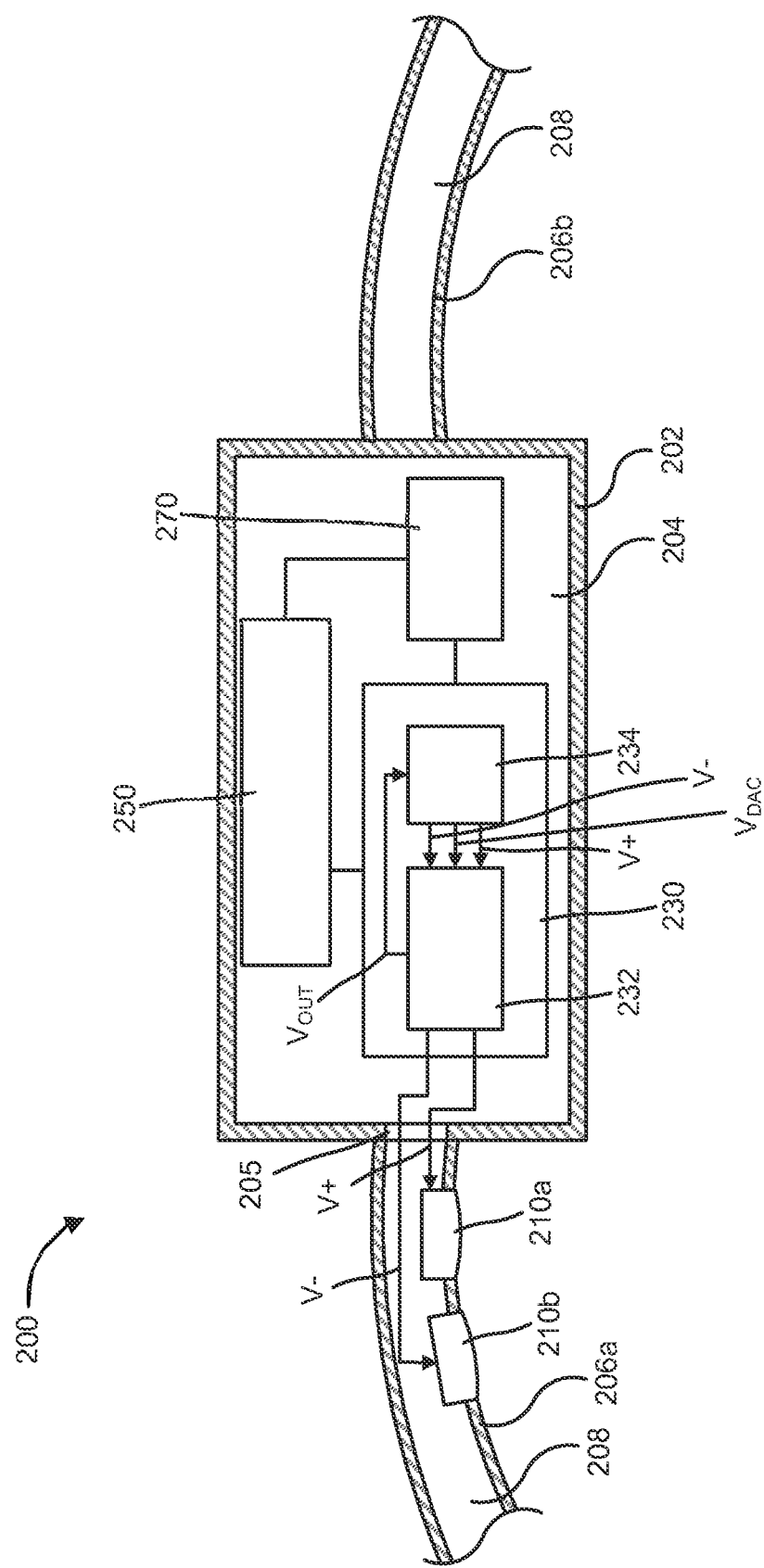
FIG. 5 shows a cross-sectional side view of the wearable device of FIG. 3 taken along the line 5-5 shown in FIG. 4.

In some embodiments, an apparatus for measuring electrodermal activity can include a first electrode and a second electrode. Referring now to FIG. 3, an apparatus 100 for measuring the electrodermal activity includes a first electrode 110a, a second electrode 110b (collectively referred to as "the electrodes 110") and a processing module 130. The first electrode 110a and the second electrode 110b can be disposed on a stratum corneum SC of a skin of a target, such that the first electrode 110a and the second electrode 110b can be in electronic communication through the stratum corneum SC and measure a conductance of the stratum corneum SC.

The electrodes 110 can include any suitable electrodes that can allow electronic communication through the stratum corneum SC and measure a conductance of the stratum corneum SC. For example, the first electrode 110a can be brought into contact with a first portion of the stratum corneum SC of the skin, and the second electrode 110b can be brought into contact with a second portion of the stratum corneum SC, such that the first electrode 110a is in electronic communication with the second electrode 110b through the stratum corneum SC. The electrodes 110 can have any suitable shape. For example, the electrodes 110 can be discs, plates, or rods, a solid state microfabricated electrode (e.g., of the type used in MEMS devices), or a screen printed electrode. The electrodes 110 can have any suitable cross section, for example circular, square, rectangle, elliptical, polygonal, or any other suitable cross-section. In some embodiments, at least a portion of the electrodes 110 can be insulated with an insulating material, for example, rubber, TEFLON®, plastic, parylene, silicon dioxide, silicon nitride, any other suitable insulation material or combination thereof. The insulation material can, for example, be used to define an active area of the electrodes 110. In some embodiments, the electrodes 110 can be subjected to a surface modification process to modify a surface area of the electrodes 110, for example, to provide a larger surface area. Such surface modification processes can include, for example, etching (e.g., etching in an acidic or basic solution), voltage cycling (e.g., cyclic voltammetry), electrodeposition of nanoparticles, and/or any other suitable surface modification process or combination thereof The electrodes 110 can be formed from any suitable material capable of electronic communication (i.e., ionic and electric communication) through the stratum corneum. Suitable materials can include, for example, silver (Ag), gold, platinum, palladium, iridium, carbon, graphite, carbon nanotubes, graphenes, conductive polymers, ceramics, alloys, any other suitable material or combination thereof. In some embodiments, the electrodes 110 can include Ag electrodes, for example, metallic plates coated with Ag. The Ag electrodes can dissociate into $Ag^+$ ions at the surface of the electrode allowing electronic communication through the stratum corneum. Ag can also prevent any damage to the stratum corneum and has inherent anti-bacterial properties that can prevent any bacterial growth on the stratum corneum in proximity of the electrodes 110.

The processing module 130 is coupled to the first electrode 110a and the second electrode 110b. The processing module 130 can be operable to (a) bias the first electrode at a first voltage V+ and the second electrode at a second voltage V−, (b) measure a current flowing between the first electrode and the second electrode, the current corresponding to the conductance of the stratum corneum, (c) subtract a compensation current from the measured current, (d) measure a resulting current and produce an amplified output voltage, (e) measure a conductance of the stratum corneum, and (f) adjust at least one of the first voltage, the second voltage and the compensation current to desaturate the output voltage.

In some embodiments, the processing module 130 can include an electrical circuit (not shown) configured to polarize the first electrode 110a at the first voltage and the second electrode 110b at the second voltage. The electrical circuit can include a resistor and an amplifier, for example, an operational amplifier, a transimpedance amplifier, a voltage amplifier, a current amplifier, a transconductance amplifier, any other suitable amplifier or combination thereof. The electrical circuit can be further configured to measure a conductance (e.g., the tonic level conductance and/or the phasic level conductance of the stratum corneum SC) and an output voltage which corresponds to the conductance of the stratum corneum SC.

The processing module 130 can also include a compensation mechanism (not shown) configured to communicate a compensation voltage to the electrical circuit to modify the compensation current or modify the difference in voltage between the two electrodes. The compensation mechanism can be configured to optimally measure the current flowing between the first electrode and the second electrode, corresponding to the conductance of the stratum corneum. Furthermore, the compensation mechanism can be configured to adjust at least one of the first voltage and the second voltage, or to adjust the compensation current if the output voltage reaches a saturation value, for example a high saturation or a low saturation. Moreover, the compensation mechanism can be configured to adjust the compensation current if the conductance of the stratum corneum SC is too low. For example, the compensation mechanism can be configured to increase the compensation current if the output voltage reaches a saturation value or decrease the compensation current if the conductance of the stratum corneum is too low. In this manner, the compensation mechanism can serve as voltage feedback mechanism to maintain the output voltage at an optimal value.

In some embodiments, the processing module 130 can include a filtering circuit, for example, a low pass filter, a high pass filter, a band pass filter, any other suitable filtering circuit, or combination thereof, configured to substantially reduce signal noise. In some embodiments, the processing module 130 can include a processor, for example, a microcontroller, a microprocessor, an ASIC chip, an ARM chip, or a programmable logic controller (PLC). The processor can include signal processing algorithms, for example, band pass filters, and/or any other signal processing algorithms or combination thereof. In some embodiments, the processing module 130 can include a memory configured to store at least one of an electrodermal activity data, or a physiological status data, for example, ANS activity data. In some embodiments, the memory can also be configured to store a reference signature, for example, a calibration equation. In such embodiments, the processor can include algorithms which can be configured to correlate the measured electrodermal activity data to an ANS activity or any other physiological status parameter of the user. The memory can also include algorithms to maximize the signal to noise ratio of the electrodermal activity signal. In some embodiments, the processing module 130 can also include a generator of clock signals coupled to the processor. In some embodiments, the processing module 130 can also include an RFID or bluetooth chip configured to store or send information in real-time for example, the electrodermal activity data, and allow a near field communication (NFC) device to read the stored information.

In some embodiments, the processing module 130 can be configured to measure a compensated value of conductance from which a tonic level conductance is removed. In some embodiments, the processing module 130 can be configured to reverse a polarity of the at least one of the first electrode 110 and the second electrode 110b after a predetermined period of time to substantially reduce electrolysis. For example, reversing the plurality can urge any dissolved ions of the electrodes 110, for example, $Ag^+$ ions to be reabsorbed into the electrodes 110. This can reduce fouling of the electrodes 110, increase shelf life, and/or prevent irritation of the skin. In some embodiments, the processing module can be configured to allow a tuning of the compensation current that is subtracted from the current flowing between the electrodes before the current is amplified. For example, the processing module 130 can be configured to allow a tuning of the current corresponding to the conductance of the stratum corneum SC in the range of about −1 μA to about 1 μA. The apparatus 100 can be configured to measure a conductance of a stratum corneum SC of any portion of the skin of the use, for example, the skin of a wrist of a user. In such embodiments, the processing module 130 can be configured to measure a tonic level conductance of the stratum corneum SC of the wrist in the range of about 0.05 μS to about 80 μS. In some embodiments, the apparatus 100 can be configured to measure a conductance of a stratum corneum of a finger of a user. In such embodiments, the processing module 130 can be configured to measure a tonic level conductance of the stratum corneum SC of the finger in the range of about 0.5 μS to about 50 μS. In some embodiments, the processing module 130 can be configured to measure a phasic level conductance of up to about 5 mS. In some embodiments, the apparatus 100 can be configured to measure the conductance of the stratum corneum with a resolution of 0.0001 μS.

In some embodiments, the apparatus 100 can also include a communications module (not shown) coupled to the processing module 130. The communications module can be configured to display an electrodermal activity of the user or communicate electrodermal activity data from the processing module 130 to an external device, for example, a smart phone app, a local computer and/or a remote server. In some embodiments, the communications module includes a communication interface to provide wired communication with the external device, for example, a USB, USB 2.0, or fire wire (IEEE 1394) interface. In some embodiments, the communication interface can also be used to recharge a power source (not shown), for example, a rechargeable battery which can be included in the apparatus 100. The power source can include for example, coin cells, Li-ion or Ni-Cad batteries of the type used in cellular phones. In some embodiments, the communications module can include means for wireless communication with the external device, for example, Wi-Fi, BLUETOOTH®, low powered BLUETOOTH®, Wi-Fi, Zigbee and the like.

In some embodiments, the communications module can include a display, for example, a touch screen display, configured to communicate information to the user for example, electrodermal activity, ANS activity, physiological activity of use, remaining battery life, wireless connectivity status, time, date, and/or user reminders. In some embodiments, the communications module can also include microphones and/or vibration mechanisms to convey audio and tactile alerts. In some embodiments, the communications module can include a user input interface, for example, a button, a switch, an alphanumeric keypad, and/or a touch screen, for example, to allow a user to input information into the dose measurement system 100, for example, power ON the system, power OFF the system, reset the system, manually input details of a user behavior, manually input details of apparatus 100 usage and/or manually initiate communication between the apparatus 100 and a remote device.

In some embodiments, the apparatus can also include various physiological sensors, for example, a heart beat sensor (e.g., a photoplethysmography sensor), an accelerometer, a temperature sensor, a blood oxygen sensors, a glucose sensor, a barometer, a gyroscope, any other physiological sensor or combination thereof. In such embodiments, the processing module 130 can be configured to process signals form each sensor to determine a physiological status of the user. In some embodiments, data processing of the signal received from each sensor can be performed on an external device, for example, a smart phone, a tablet, a personal computer, or a remote server. Furthermore, the communications module can be configured to communicate the physiological data from each of the sensors to the user, for example, via a display included in the apparatus or the external device. Such physiological data can include, for example, electrodermal activity (e.g., skin conductance), heart rate, heart rate variability, metabolic equivalent of task (MET), a stress level, a relaxation level, a movement or activity level, a temperature, a heat flux, and/or an ANS activity (e.g., an arousal or excitement).

In some embodiments, the apparatus can include a housing (not shown) which can be configured to removably associate with the stratum corneum SC of the user. The housing can define an internal volume within which the electrodes 110, the processing module 130, the communications module, and the power source, and/or any other components included in the apparatus 100 can be disposed. At least a portion of the first electrode 110a and the second electrode 110b can be disposed outside the housing. The electrodes 110 can be configured such that the first electrode 110 contacts a first portion of the stratum corneum SC and the second electrode 110b contacts a second portion of the stratum corneum SC when the housing is associated with the skin of the user.

The housing can be formed from a material that is relatively lightweight and flexible, yet sturdy. The housing also can be formed from a combination of materials such as to provide specific portions that are rigid and specific portions that are flexible. Example materials include plastic and rubber materials, such as polystyrene, polybutene, carbonate, urethane rubbers, butene rubbers, silicone, and other comparable materials and mixtures thereof, or a combination of these materials or any other suitable material can be used. The housing can have a relatively smooth surface, curved sides, and/or otherwise an ergonomic shape.

In some embodiments, the apparatus 100 can have a small form factor such that the apparatus 100 is wearable (i.e., can be worn on a body part of a user). For example, in some embodiments, the apparatus 100 can be a wrist band. In such embodiments, a flexible strap, for example, leather strap, a rubber strap, a fiber strap, or a metal strap can be coupled to the housing and configured to secure the housing to the body part of the user. Furthermore, the housing can have a small form factor. In some embodiments, the strap can be hollow such that the strap defines an internal volume. In such embodiment, any one of the sensors included in the apparatus 100, for example, the electrodes 110 configured to measure electrodermal activity can be disposed in the internal volume defined by the strap. At least a portion of the electrodes 110 can be disposed outside the housing to contact the stratum corneum SC of the skin of the user. In some embodiments, the apparatus 100 can be a head band, an arm band, a foot band, an ankle band, or a ring. In some embodiments, the apparatus 110 can be a glove configured to be worn on a hand of the user.

In use the apparatus 100 can be disposed on the skin of a user such that the first electrode 110a contacts a first portion of the stratum corneum SC of the skin (e.g., the skin of a wrist of the user), and the second electrode 110b contacts a second portion of the stratum corneum SC. The processing module 130 can bias the first electrode at a first voltage and the second electrode at a second voltage different than the first voltage, and measure a skin current flowing through the stratum corneum. A compensation current can be subtracted from the skin current to obtain an input current. The compensation current can be set by a compensation voltage, for example, a compensation voltage provided by the compensation mechanism. The processing module 130 can transform the input current to measure an output voltage and a conductance of the stratum corneum SC (e.g., derived from the output voltage). The processing module 130 can determine if the output voltage is saturated or unsaturated. If the output voltage is saturated, for example, saturated high or saturated low, the processing module 130 can adjust the first voltage, the second voltage and/or the compensation current (e.g., by adjusting the compensating voltage) to desaturate the output voltage. The apparatus 100 can be configured to perform real time measurements of the electrodermal activity and/or any other physiological parameters such that a physiological status of the user can be determined. This information can be used to generate a physiological profile of the user over a period of time.

Having described above various general principles, several embodiments of these concepts are now described. These embodiments are only examples, and many other configurations of systems, devices and methods for measuring electrodermal activity are contemplated.

In some embodiments, an apparatus for measuring electrodermal activity can include a wearable device configured to be worn on the wrist of a user. Referring now to FIGS. 4-7, a wearable device 200 for measuring electrodermal activity includes a housing 202, a first strap 206a and a second strap 206b, a first electrode 210a, a second electrode

210b (collectively referred to as the "electrodes 210"), a processing module 230, a communications module 250, and a power source 270. The wearable device 200 is configured to be worn on the wrist of the user, analogous to a watch and to measure at least an electrodermal activity of the stratum corneum of a skin on the wrist of the user.

The housing 202 defines an internal volume 204 configured to house the processing module 230, the communications module 250 and the power source 270. The housing 202 can be formed from a material that is relatively lightweight and flexible, yet sturdy. The housing 202 also can be formed from a combination of materials such as to provide specific portions that are rigid and specific portions that are flexible. Example materials include plastic and rubber materials, such as polystyrene, polybutene, carbonate, urethane rubbers, butene rubbers, silicone, and other comparable materials and mixtures thereof, or a combination of these materials or any other suitable material can be used. The housing 202 can have a relatively smooth surface, curved sides, and/or otherwise an ergonomic shape. While shown as being a monolithic structure, in some embodiments, the housing 202 can include a base and a cover such that the base is removably coupled to the cover to define the internal volume 204. In some embodiments, the base can be removed to access the components disposed in the housing 204 (e.g., the replace the power source 270).

A first strap 206a and a second strap 206b (collectively referred to as the "straps 206") are coupled to a first side and a second side of the housing 202, respectively. The straps 206 can be formed from any suitable material such as, for example, leather, rubber, fiber, polyurethane, or metal. The straps 206 can include a coupling mechanism, for example, a hole and pin, clamp, notches, grooves, indents, detents, magnets, Velcro, bands, or any other suitable coupling mechanism to couple the straps 206 to each other. In this manner, the strap 206 can be removably secured on the wrist of the user such that the electrodes 210 can be associated with stratum corneum of the wrist of the user. Each strap 206 defines an internal volume 208 which is coupled to the housing 202 via an opening 205 defined in a side wall of the housing 202. The opening can allow the processing module 230 to be electrically coupled to the electrodes 210 via electrical couplings, for example, electrical leads, that can pass through the opening 205 between the internal volume 204 of the housing 202, and the internal volume 208 of the strap 206. The electrodes 210 are disposed in the internal volume 208 defined by the first strap 206a such that at least a portion of each of the electrodes 210 is disposed outside the internal volume. In this manner, the electrodes 210 are configured to contact the stratum corneum of the skin of the user when the wearable device 200 is associated with the wrist of the user.

The electrodes 210 can includes any suitable electrodes that can allow electronic communication through the stratum corneum and measure a conductance of the stratum corneum. For example, the first electrode 210a can be brought into contact with a first portion of the stratum corneum of the skin, and the second electrode 210b can be brought into contact with a second portion of the stratum corneum of the skin, such that the first electrode 210a is in electronic communication with the second electrode 210b through the stratum corneum. The electrodes 210 can have any suitable shape. While shown as having at least one surface which is curved, the electrodes 210 can have any suitable shape For example, the electrodes 210 can be discs, plates, or rods, a solid state microfabricated electrode (e.g., of the type used in MEMS devices), or a screen printed electrode. The electrodes 210 can have any suitable cross section, for example circular, square, rectangle, elliptical, polygonal, or any other suitable cross-section. In some embodiments, at least a portion of the electrodes 210 can be insulated with an insulating material, for example, rubber, TEFLON®, plastic, parylene, silicon dioxide, silicon nitride, any other suitable insulation material or combination thereof. The insulation material can, for example, be used to define an active area of the electrodes 210. In some embodiments, the electrodes 210 can be subjected to a surface modification process to modify a surface area of the electrodes 210 for example, to provide a larger surface area. Such surface modification processes can include, for example, etching (e.g., etching in an acidic or basic solution), voltage cycling (e.g., cyclic voltammetry), electrodeposition of nanoparticles, and/or any other suitable surface modification process or combination thereof The electrodes 210 can be formed from any suitable material capable of electronic communication (i.e., ionic and electric communication) through the stratum corneum. Suitable materials can include, for example, silver (Ag), gold, platinum, palladium, rhodium, iridium, carbon, graphite, carbon nanotubes, graphenes, conductive polymers, ceramics, alloys, any other suitable material or combination thereof. In some embodiments, the electrodes 210 can include Ag electrodes, for example, metallic plates coated with Ag. The Ag electrodes can dissociate into $Ag^+$ ions at the surface of the electrode allowing that can exchange ions with the electrolytes included in the sweat produced on the stratum corneum, thereby allowing electronic communication through the stratum corneum. Ag can also prevent any damage to the stratum corneum and has inherent antibacterial properties that can prevent any bacterial growth on the stratum corneum in proximity of the electrodes 210.

The processing module 230 is disposed in the internal volume 204 defined by the housing 202. The processing module 230 includes an electrical circuit 232 and a compensation mechanism 234. The electrical circuit 232 can include an amplifier A, for example, an operational amplifier, a transimpedance amplifier, a voltage amplifier, a current amplifier, a transconductance amplifier, a transimpedance amplifier, any other suitable amplifier or combination thereof. The electrical circuit 232 also includes an analog to digital converter (ADC). The electrical circuit 232 can be configured to measure and output voltage $V_{OUT}$ and obtain the conductance of the stratum corneum from the output voltage $V_{OUT}$ as described herein. The compensation mechanism 234 can include at least a digital to analog converter. The compensation mechanism can be configured to read the output voltage $V_{OUT}$ and set a compensation voltage $v_{BAC}$ corresponding to a compensation current $I_{comp}$ as described herein.

In some embodiments, the processing module 230 can also be configured to reverse a polarity of the at least one of the first electrode 210a and the second electrode 210b after a predetermined period of time to substantially reduce electrolysis. For example, reversing the plurality can urge any dissolved ions of the electrodes 210, for example, $Ag^+$ ions to reabsorb into the electrodes 210. This can, for example, reduce fouling of the electrodes 210, increase shelf life, and/or prevent irritation of the skin.

Figure 6:
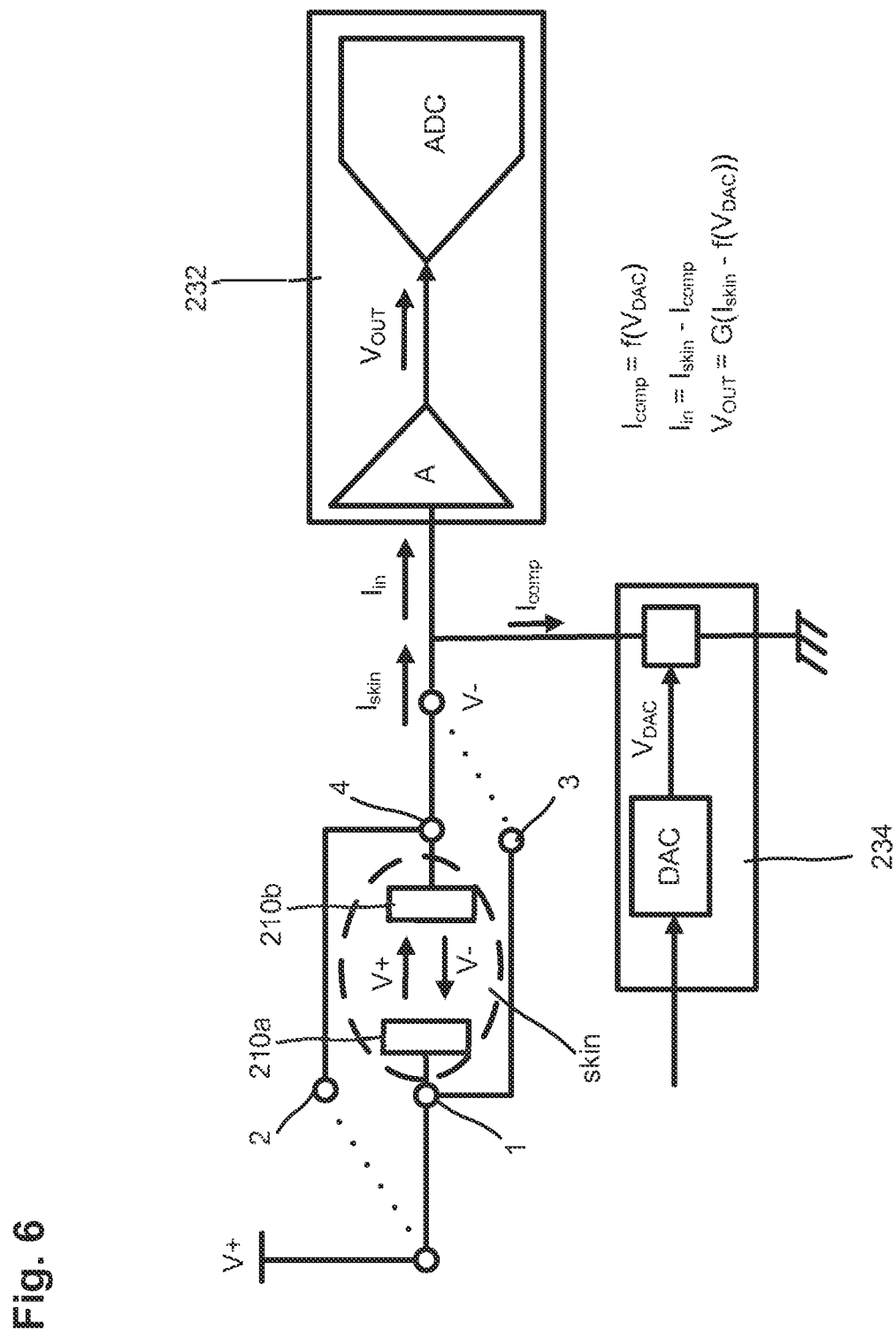
FIG. 6 shows a circuit diagram of a processing module included in the wearable device of FIG. 3 that can be used for current compensation and polarity inversion.

FIG. 6 shows a circuit diagram of the processing module 230 that can be used for current compensation and polarity inversion. As shown in FIG. 6, the electrodes 210 can be in contact with the skin, for example, the stratum corneum of the skin. The stratum corneum acts as a variable resistor disposed between the electrodes 210. The conductance of the stratum corneum changes as the thickness of the stratum corneum changes, for example, because of a change in the physiological status of the user.

Figure 7:
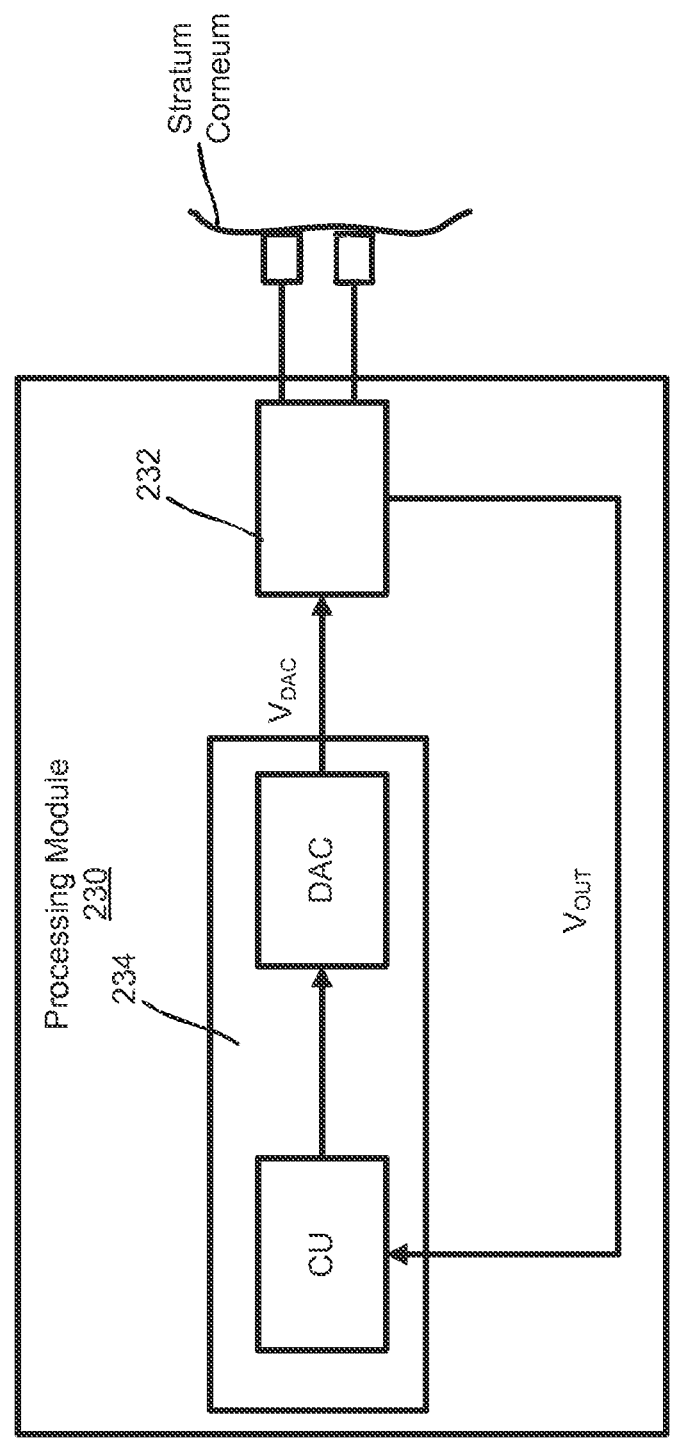
FIG. 7 shows an overall schematic diagram of a processing module included in the wearable device of FIG. 3.

The power source 270 can be used to provide a positive voltage V+ at a first node 1 and a negative voltage V− at a third node 3. In this configuration, the first electrode 210a receives the positive voltage V+ and the second electrode 210b receives the negative voltage V−. A polarity inversion mechanism, for example, a directional switch, can be used to divert the positive voltage towards a second node 2 and the negative voltage towards a fourth node 4. As shown in FIG. 7, this reverses the polarity of the electrodes 210, such that the first electrode 210a is now biased at the negative voltage V− and the second electrode 210b is biased at the positive voltage V+.

As shown in FIG. 6, the digital to analog converter (DAC) included in the compensation mechanism 234 is configured to subtract a compensation current $I_{comp}$ from entering the amplifier A. Thus the input current $I_{in}$ entering the amplifier A is;

$$I_{in}=I_{skin}-I_{comp}$$

The DAC produces a voltage $V_{DAC}$ such that the compensation current $I_{comp}=f(V_{DAC})$, where f is a quasilinear function.

The amplifier A is responsible for amplifying the current $I_{in}$ for a given gain G and transform the input current $I_{in}$ into the output voltage $V_{OUT}$. The output voltage $V_{OUT}$ is used to obtain a conductance of the stratum corneum. The processing module 230 also includes an analog to digital converter (ADC) configured to convert the analog signal to a digital signal. The ADC can have any suitable resolution, for example, 10 bits, 12 bits or 16 bits. The gain G of the amplifier A can be fixed and chosen to meet the range requirements of the conductance levels of skin such that the output voltage $V_{OUT}$ after the gain G is, $$V_{out}=G(I_{skin}-f(V_{DAC}))$$

FIG. 7 shows an overall schematic of the processing module 230. The control unit CU included in the compensation mechanism 234 sets a value of the compensation voltage $V_{DAC}$ and reads the output voltage $V_{OUT}$ of the electrical circuit 232. Since the gain G of the amplifier A is substantially high to magnify the weak conductance signal obtained from the electrodes 210, $V_{OUT}$ tends to saturate towards a maximum value $V_{MAX}$ or 0. When this happens, the control unit CU acts on the compensation voltage $V_{BAC}$ in order to de-saturate the output voltage $V_{OUT}$. For instance, if the skin conductance keeps increasing the output voltage $V_{OUT}$ will saturate. The compensation mechanism 234 can then increase the compensation current $I_{comp}$ to reduce the output voltage $V_{OUT}$ to a readable range.

Figure 8:
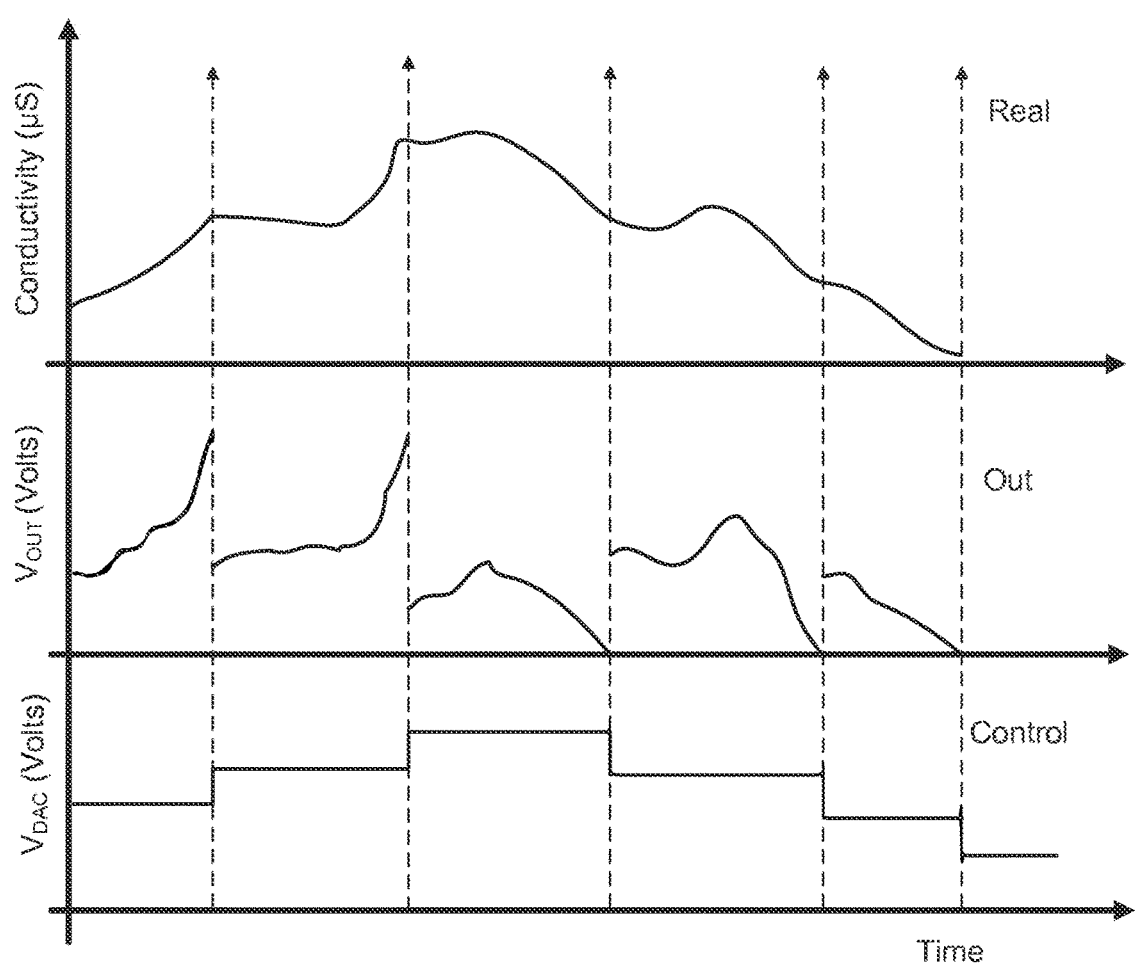
FIG. 8 is a plot showing the electrodermal activity sensing performance of the wearable sensor including a real conductance level, an output voltage $V_{OU}$, and a compensation voltage $V_{DAC}$.

This concept is further illustrated in FIG. 8. The top panel of FIG. 8 shows real time conductance of the stratum corneum which includes the tonic and the phasic levels. The middle panel shows the output voltage $V_{OUT}$ measured by the electrical circuit 232, and the bottom panel shows the compensation voltage $V_{DAC}$ set by the control unit CU. The electrodes 210 can be initialized at an initial value of the compensation voltage $V_{DAC}$. The magnitude of the output voltage $V_{OUT}$ can be measured by the compensation mechanism 234. As soon as the conductance increases and the output voltage $V_{OUT}$ increases and eventually reaches its saturation value (e.g., about 3.3 volts). In this scenario a substantial amount of current is flowing through the stratum corneum. To avoid saturation, the compensation mechanism 234 can compensate for the current by increasing the compensation voltage $V_{DAC}$. This allows a higher current to flow away from the amplifier A and thereby, leads to desaturation of the output voltage $V_{OUT}$. On the other hand when the conductance decreases the output voltage $V_{OUT}$ also decreases until the output voltage $V_{OUT}$ falls below a predetermined threshold, for example, the electrical circuit 232 fails to read the output voltage $V_{OUT}$. In this scenario, the compensation mechanism 234 can decrease the compensation voltage $V_{DAC}$, thereby allowing more current to flow towards the amplifier A and increasing the magnitude of the output voltage $V_{OUT}$. In this manner, the compensation mechanism 232 can be configured to dynamically set the compensation value for the tonic level conductance that is subtracted from the real conductance level. Thus, when the wearable device 100 is in a stable state, the compensation voltage $V_{DAC}$ is proportional to the current tonic level conductance of the user. The compensation mechanism 234 can measure the entire range of tonic level conductances associate with the stratum corneum of the wrist of the user, for example, in the range of about 0.05 μS to about 80 μS. In some embodiments, the compensation mechanism can allow a fine tuning of the current in the range of about −1 μA to about 1 μA.

Furthermore, the compensation mechanism 234 allows for the subtraction of the tonic level from the real time conductance such that the output voltage $V_{OUT}$ represents the phasic value of the electrodermal activity. Thus the phasic level conductance can be measured with high resolution, for example, by an analog to digital converter (ADC) included in the processing module 230. In some embodiments, the phasic level can be measured with a resolution of about 0.0001 μS.

In this manner, the current compensation enables the range to be increased by focusing on a dynamic portion of the total range. The compensation mechanism 234 dynamically sets the compensation current to fit the tonic level conductance while the amplifier A and the ADC observe the phasic level conductance. The gain G provided by the amplifier A and the high resolution of the ADC enables the signal to be resolved with high resolution. Furthermore, the switching mechanism reduces electrolysis of the electrodes by allowing polarity inversion of the electrodes at predetermined intervals.

While shown as including the electrical circuit 232 and the compensation mechanism 234, the processing module 230 can include any other components. In some embodiments, the processing module 230 can include a filtering circuit, for example, a low pass filter, a high pass filter, a band pass filter, any other suitable filtering circuit, or combination thereof, configured to substantially reduce signal noise. In some embodiments, the processing module 230 can include a processor, for example, a microcontroller, a microprocessor, an ASIC chip, an ARM chip, or a programmable logic controller (PLC). The processor can include signal processing algorithms, for example, band pass filters, low pass filters, any other signal processing algorithms or combination thereof. In some embodiments, the processing module 230 can include a memory configured to store at least one of an electrodermal activity data, or a physiological status data, for example, ANS activity data. In some embodiments, the memory can also be configured to store a reference signature, for example, a calibration equation. In such embodiments, the processor can include algorithms which can be configured to correlate the measured electrodermal activity data to an ANS activity or any other physiological status parameter of the user. The memory can also include algorithms to maximize the signal to noise ratio of the electrodermal activity signal. In some embodiments, the processing module 230 can also include a generator of clock signals coupled to the processor. In some embodiments, the processing module 230 can also include an RFID chip configured to store information, for example, the electrodermal activity data, and allow a near field communication (NFC) device to read the stored information.

In some embodiments, the processing module 230 can be configured to measure a compensated value of conductance from which a tonic level conductance is removed. In some embodiments, the processing module 230 can be configured to allow a tuning of the current corresponding to the conductance of the stratum corneum in the range of about −1 μA to about 1 μA. In some embodiments, the processing module 230 can be configured to measure a tonic level conductance of the stratum corneum of the wrist in the range of about 0.05 μS to about 80 μS.

The communications module 250 is coupled to the processing module 230. The communications module 250 can be configured to display an electrodermal activity of the user or communicate electrodermal activity data from the processing module 230 to an external device, for example, a smart phone app, a local computer and/or a remote server. In some embodiments, the communications module 250 includes a communication interface to provide wired communication with the external device, for example, a USB, USB 2.0, or fire wire (IEEE 1394) interface.

In some embodiments, the communications module 250 can include means for wireless communication with the external device, for example, Wi-Fi, BLUETOOTH®, low powered BLUETOOTH®, Wi-Fi, Zigbee and the like. In some embodiments, the communications module 250 can include a display, for example, a touch screen display, configured to communicate information to the user, for example, electrodermal activity, ANS activity, physiological activity of the user, remaining battery life, wireless connectivity status, time, date, and/or user reminders. In some embodiments, the communications module 250 can also include microphones and/or vibration mechanisms to convey audio and tactile alerts. In some embodiments, the communications module 250 can include a user input interface, for example, a button, a switch, an alphanumeric keypad, and/or a touch screen, for example, to allow a user to input information into the wearable device 200, for example, power ON the system, power OFF the system, reset the system, manually input details of a user behavior, manually input details of the wearable device 200 usage and/or manually initiate communication between the wearable device and the external device.

The power source 270 is coupled to the processing module 230 and the communications module 250 and configured to supply electrical power to the processing module 230 and the communications module 250. The power source can include for example, coin cells, Li-ion or Ni-Cad batteries of the type used in cellular phones. In some embodiments, the communications module 250 can also be used to recharge the power source 270, for example, by providing power to the power source 270 from an external source through a communications lead. In some embodiments, the power source 270 can be recharged using inductive coupling.

Figure 9:
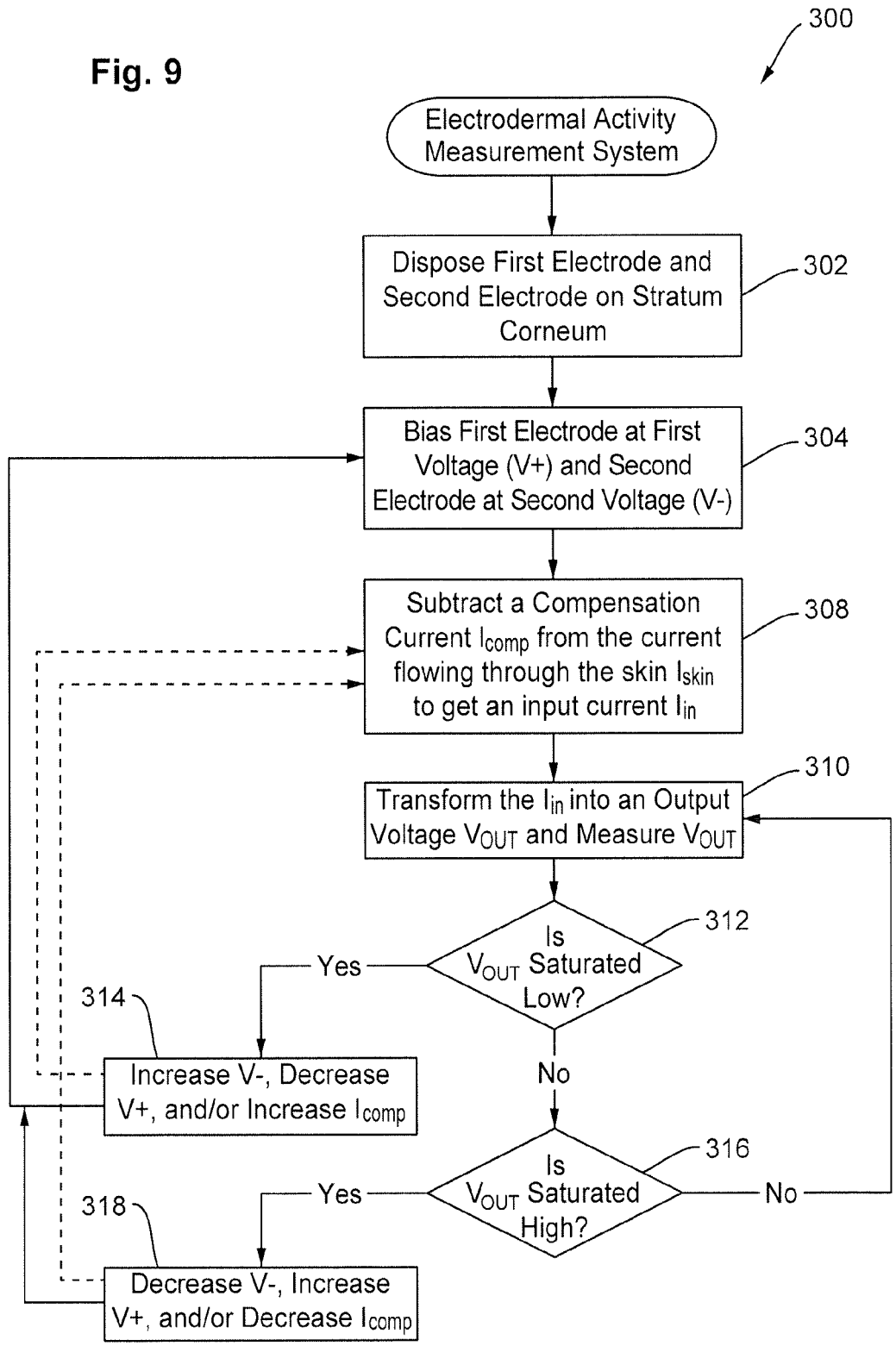
FIG. 9 shows a method of measuring electrodermal activity, according to an embodiment.

FIG. 9 shows an exemplary method 300 for measuring electrodermal activity including the tonic level and the phasic level over a wide range, for example, in the range of about 0.05 μA and 80 μA. The method 300 can be used with any electrodermal activity measurement system, for example, the apparatus 100, the wearable device 200, or any other apparatus or device described herein. The method 300 involves disposing a first electrode and a second electrode on the stratum corneum 302. The electrodes can include the electrodes 110, 210 or any other electrode described herein. The first electrode is biased at a first voltage V+ and the second electrode is biased at a second voltage V− 304. For example, the first electrode can be positively charged and the second electrode can be negatively charged or vice versa. A compensation current $I_{comp}$ is subtracted from a current $I_{skin}$ flowing through the stratum corneum to obtain an input current 308. For example, a compensation mechanism (e.g., the compensation mechanism 234 or any other compensation mechanism described herein) can be used to set a compensation voltage that is transformed into the compensation current to be subtracted from the skin current $I_{skin}$. The input current $I_{in}$, is transformed into an output voltage which is measured 310. For example, a transimpedance amplifier (e.g., a transimpedance amplifier included in the electrical circuit 232 or any other electrical circuit described herein) can be used to transform the input current into the output voltage $V_{OUT}$. The output voltage is related to a conductance of the stratum corneum and is used to measure the conductance of the stratum corneum. The method then determines if the output voltage $V_{OUT}$ is saturated low 312. For example, the output voltage $V_{OUT}$ can be communicated to a compensation mechanism (e.g., the compensation mechanism 234 or any other compensation mechanism described herein) which can determine if the output voltage $V_{OUT}$ is saturated low (i.e., reached a minimum value). In this scenario, the first voltage V+ can be decreased, the second voltage V− can be increased, or the compensation current $I_{comp}$ is increased 314 to change the output voltage $V_{OUT}$ such that the output voltage $V_{OUT}$ is not saturated low.

If the output voltage $V_{OUT}$ is not saturated low, the method determines if the output voltage $V_{OUT}$ is saturated high 316, i.e., reached very high values. For example, if the conductance of the stratum corneum is too high, the output voltage $V_{OUT}$ can drop to very high values. If the output voltage $V_{OUT}$ is saturated high, the first voltage V+ can be increased, the second voltage V− can be decreased, and/or the compensation current $I_{comp}$ can be decreased 318 to change the output voltage $V_{OUT}$ such that the output voltage $V_{OUT}$ is not saturated high. If the output voltage is not saturated low or high, the method continues to measure the output voltage $V_{OUT}$. In this manner, the method enables continuous monitoring and control of the output voltage $V_{OUT}$ such that the conductance of the stratum corneum can be measured over a wide range.

Figure 10:
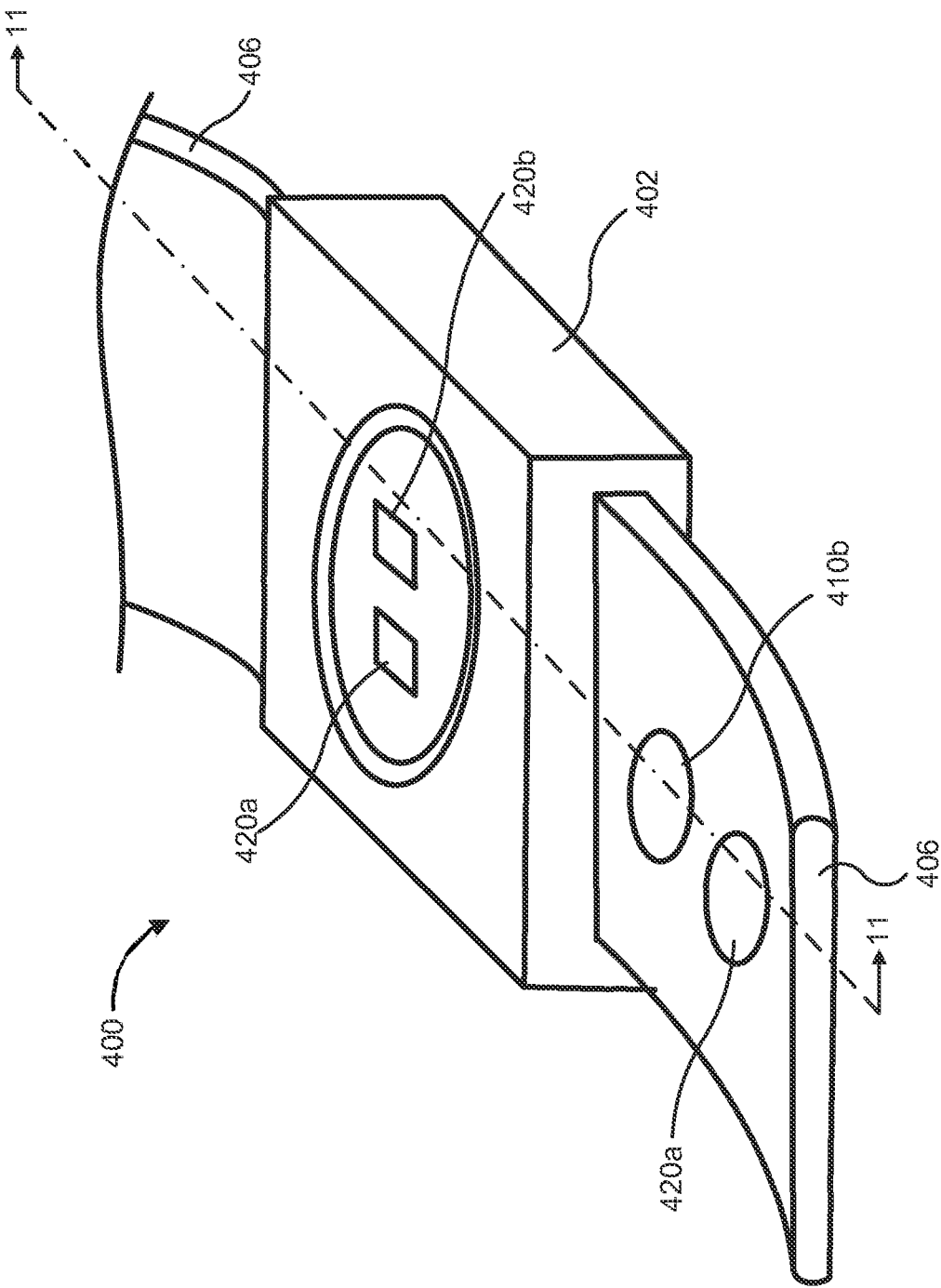
FIG. 10 shows a bottom perspective view of a wearable device that includes an electrodermal activity sensor and a heart beat sensor, according to an embodiment.
Figure 11:
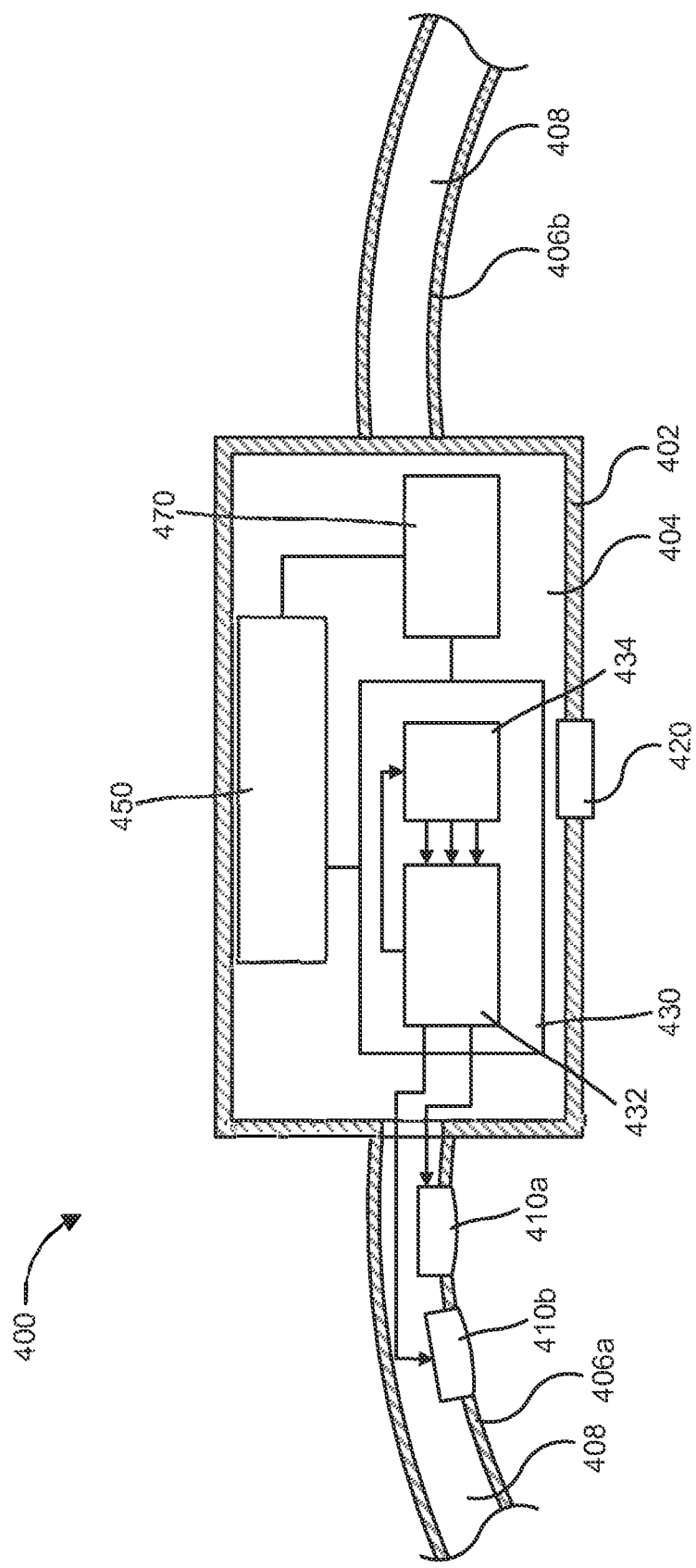
FIG. 11 shows a cross-sectional side view of the wearable device of FIG. 10 taken along the line 11-11 shown in FIG. 10.

In some embodiments, a wearable device can include an electrodermal activity sensor and a heart beat sensor. Referring now to FIGS. 10 and 11, a wearable device 400 includes a housing 402, a first strap 406a, a second strap 406b, a first electrode 410a, a second electrode 410b (collectively referred to as the "electrodes 410"), a pair of heart beat sensors 420, a processing module 430, a communications module 450, and a power source 470. The wearable device 400 is configured to be worn on the wrist of a user, analogous to a watch and to measure an electrodermal activity of the stratum corneum skin as well as the heart beat variability of the user.

The housing 402 defines an internal volume 404 configured to house at least a portion of the heart beat sensors 420, the processing module 430, the communications module 450 and the power source 470. The housing 470 can be substantially similar to the housing 470 described with respect to the wearable device 200, and is therefore not described in further detail herein.

The first strap 406a and the second strap 406b (collectively referred to as the "straps 406") are coupled to a first side and a second side of the housing 402 respectively. The straps 406 define an internal volume 408. At least a portion of the electrodes 410 can be disposed in the internal volume 408. The straps 406 can be substantially similar to the straps 406 described with reference to the wearable device 200, and are therefore not described in further detail herein.

The electrodes 410 can include any suitable electrodes that can allow electronic communication through the stratum corneum and measure a conductance of the stratum corneum. The electrodes 410 can be configured to measure an electrodermal activity of the stratum corneum of the user. The electrodes 410 can be substantially similar to the electrodes 210 described with respect to the wearable device 200, and are therefore not described in further detail herein.

The heart beat sensors 420 can be disposed in the internal volume defined by the housing 402. The heart beat sensors 420 can be any suitable sensors. In some embodiments, the heart beat sensors 420 can include electrodes such as those included in EKG monitors. In some embodiments, the heart beat sensors 420 can include optical sensors. For example, the heart beat sensors can include a light emitter and a light receiver that can convert reflected light form the skin, or blood below the skin into an electrical signal corresponding to the heart beat of the user. In some embodiments, the light emitter can include an LED diode. In some embodiments, the light receiver can include a photodiode or a phototransistor. The electrical signal measured by the light detector which corresponds to the light reflected from the skin, can be communicated to the processing module 430 for calculating a heart rate of the user. In some embodiments, the wearable device 400 can also include optical filters, for example, monochromators to dynamically select a wavelength of the reflected light. In some embodiments, the monochromators can be tunable Fabry-Perot filters.

The processing module 430 is disposed in the internal volume 404 defined by the housing 402. The processing module 430 includes an electrical circuit 432 and a compensation mechanism 434. The electrical circuit 432 and the compensation mechanism 434 can be substantially similar to the electrical circuit 232 and the compensation mechanism 234 described with respect to the wearable device 200, and are therefore not described in further detail herein. In some embodiments, the processing module 430 can include a circuit to control the electrical power communicated to the light emitter, for example, to control a luminosity of the light emitted by the light emitter included in the heart beat sensors 420.

In some embodiments, the apparatus can also include various physiological sensors, for example, a heart beat sensor (e.g., a photoplethysmography sensor), an accelerometer, a temperature sensor, a blood oxygen sensors, a glucose sensor, any other physiological sensor or combination thereof. In such embodiments, the processing module 430 can be configured to process signals form each sensor to determine a physiological status of the user. In some embodiments, data processing of the signal received from each sensor can be performed on an external device, for example, a smart phone, a tablet, a personal computer, or a remote server. Furthermore, the communications module can be configured to communicate the physiological data from each of the sensors to the user, for example, via a display included in the apparatus or the external device. Such physiological data can include, for example, electrodermal activity (e.g., skin conductance), heart rate, heart rate variability, metabolic equivalent of task (MET), a stress level, a relaxation level, a movement or activity level, a temperature, a heat flux, and/or an ANS activity (e.g., an arousal or excitement).

Figure 12:
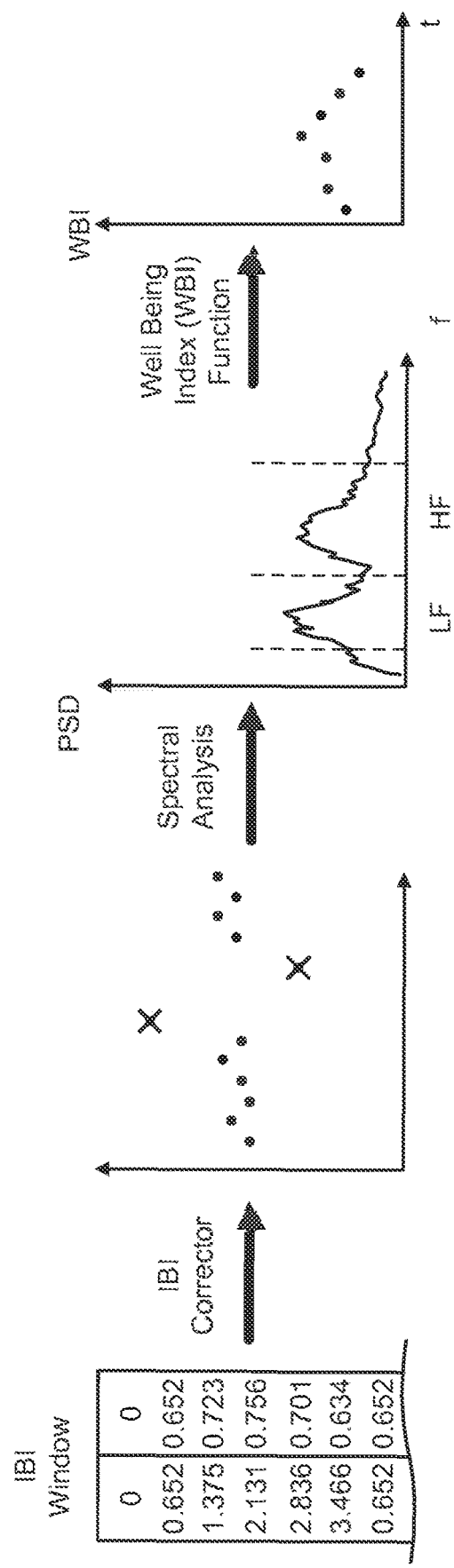
FIG. 12 shows a method for determining human well being using heart rate variability measured by a wearable activity sensor, according to an embodiment.

In some embodiments, the processing module 430 can include algorithms to determine a well being index (WBI) of the user from the HRV data. FIG. 12 shows a method that can be incorporated into an algorithm to determine a WBI of the user from the heart rate variability data. In the first step, the inter beat interval (IBI) time series is processed to identify and delete wrongly recognized and ectopic beats. In the next step, a spectral analysis of the corrected time series is performed to assess the total power, the high frequency power and the low frequency power of the cardiac rhythm. In the third step, the values obtained are given as input to the WBI function together with other cardiac parameters, and in the fourth step a WBI of the user is determined.

As described herein, the IBI time series is processed in the first step. The first column of the time series shown in FIG. 12 includes the time stamps at which the heart beat occurred. The second column includes the time interval between each subsequent heart beat. In other words, the first column is a cumulative sum of the first column. The obtained IBI time series is split into subsequent windows of five minutes.

Figure 13:
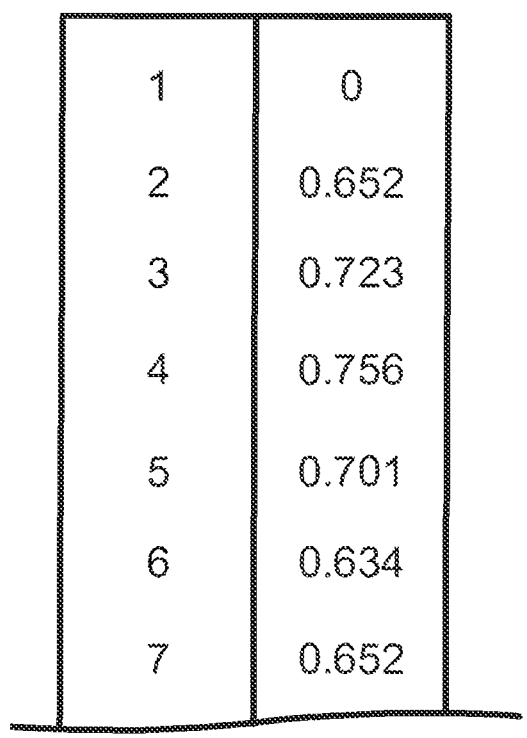
FIG. 13 shows an inter-beat interval (IBI) time series.

Errors in the location of the instantaneous heart beat can translate into errors in the calculation of the HRV. HRV is highly sensitive to artifact and errors in 2% to 5% of the data can result in unwanted biases in HRV calculations. To ensure accurate results, it is critical to manage artifacts and ectopic heart beats appropriately prior to performing any HRV analysis. To ensure accuracy, the method applies four parallel filters to the five minute IBI windows. The filters are applied to the second column of the IBI time series, assigning progressive natural numbers to the beats, as shown in FIG. 13.

The first filter includes a plain selection filter. The tachogram is initially filtered by a low-pass numerical filter. Beats falling outside a confidence region A centered in the filtered curve are discarded. The mean IBI equals the mean values of the IBI calculated in the window.

Figure 14:
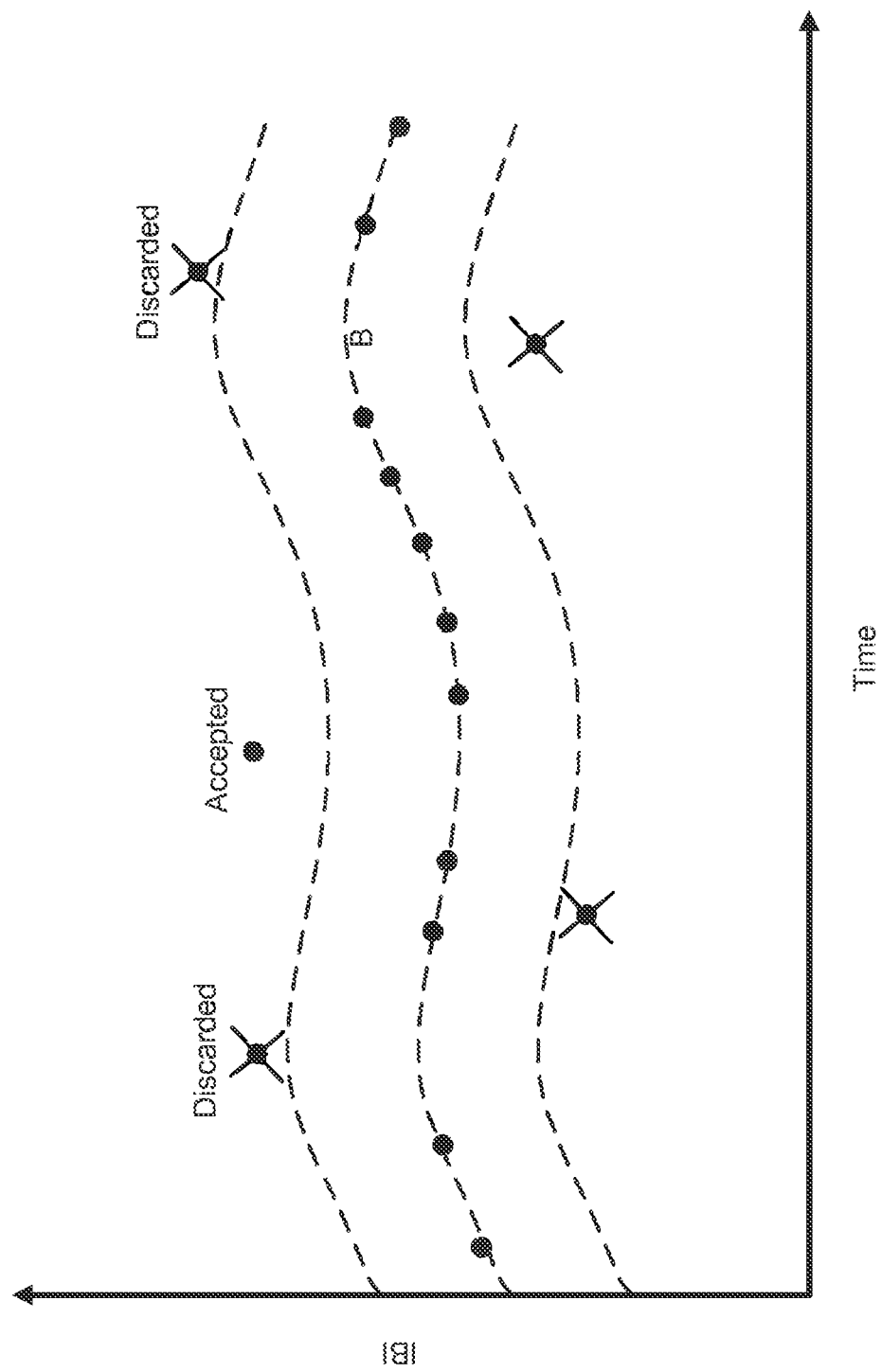
FIG. 14 shows a visual representation of a one-step selection filter for removing artifacts measured in an inter-beat interval (IBI) of heart beat.

The second filter is a one-step selection filter. A plain selection filter is first applied, with a confidence region B centered in the filtered curve, as described herein with respect to the plain selection filter. FIG. 14 shows a visual representation of the one-step selection filter. The selected beats are discarded only if subsequent points fall outside the confidence region in an opposite fashion which can happen when one beat is misrecognized.

Figure 15:
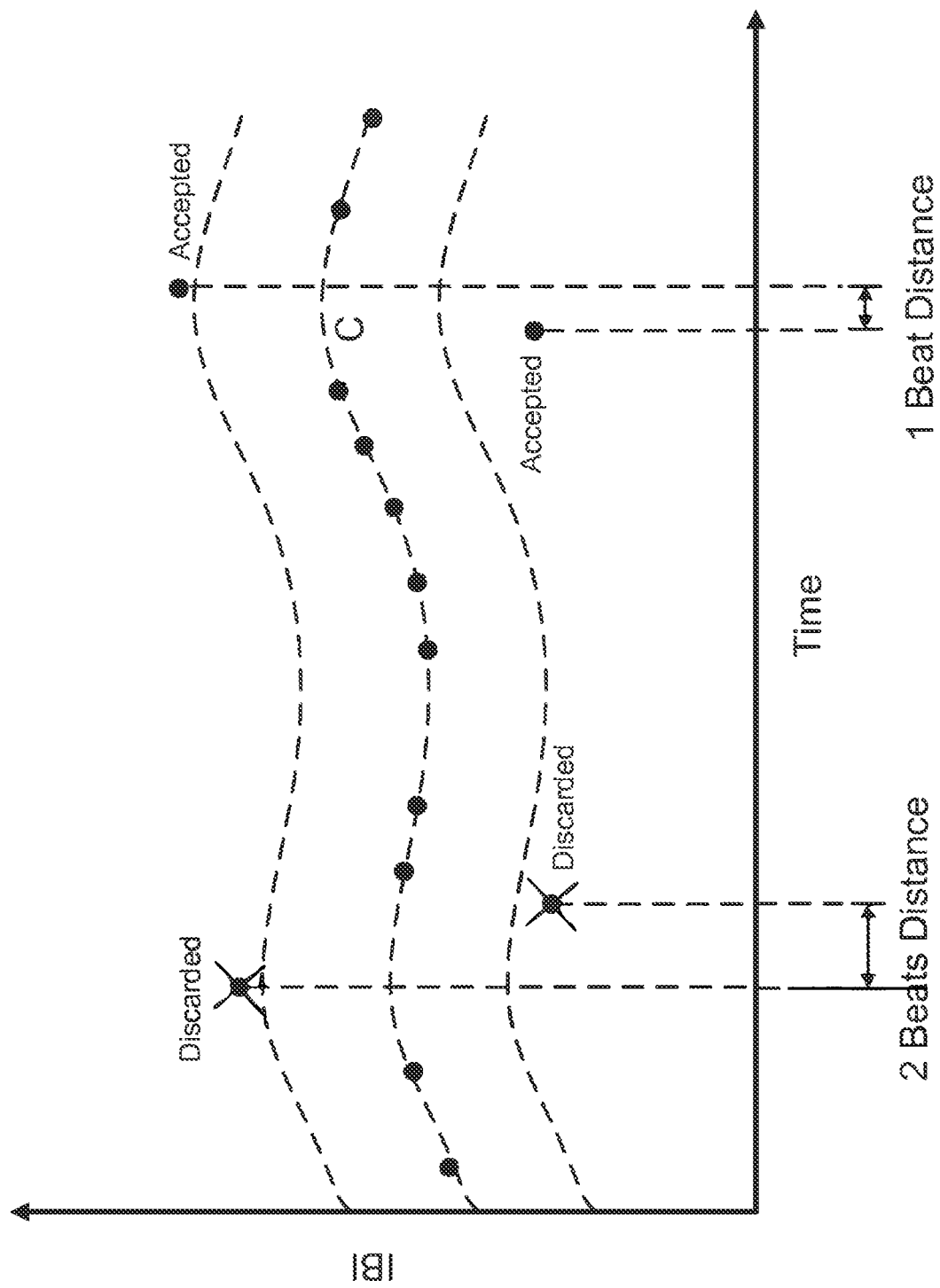
FIG. 15 shows a visual representation of a two step selection filter for removing artifacts measured in an IBI of heart beat.

The third filter is a two-step selection filter. A plain selection is first applied, with a confidence region C centered in the filtered curve, as described herein with respect to the plain selection filter. FIG. 15 shows a visual representation of the two-step selection filter. The selected beats are discarded only if points with a two beat distance fall outside the confidence region in an opposite fashion.

The fourth selection filter is a gross selection filter. First, the unit of measure of the tachogram is transformed from seconds to a heart rate measured in beats per minute (bpm), according to the following equation;

$$\text{Heart rate (hr)} = 60/\text{IBI}$$

Then a polynomial is fitted to the transformed tachogram in a least squares sense. Finally, beats that fall outside a confidence region D centered in the fitted curve are discarded.

As described herein, after the IBI time series is filtered, spectral analysis is performed on the data. Before performing the spectral analysis, the heart beat signal is detrended by applying the following equation to the second column of the windowed IBI time series;

detrended signal=constant_detrend (Hamming_window(linear_detrend(signal)))

The signal is linearly detrended before multiplying it by a hamming window of the same length. Next, a constant detrend is applied to subtract the zero frequency component. In this manner, the non-autonomic regulation of the heart rate, for example, due to vigorous exercise or voluntary physical activity is removed from the signal. Applying a hamming window to the IBI time series before the spectral analysis can thereby enhance spectral information.

A Lomb normalize periodogram is obtained which is dimensionless, and can be expressed in terms of the power spectral density (PSD) as follows:

PSD=Lomb_periodogram/integral(Lomb_periodogram)*variance(detrended signal)

The PSD equation can be applied only if the time-domain signal to be transformed has zero mean value. The integral in the equation can be a trapezoidal numerical integral.

Next, low frequency (LF), high frequency (HF), and total power (TP) values can be obtained by numerically integrating the PSD in the standard bands of 0.04 Hz to 0.15, from 0.15 Hz to 0.4 Hz, and from 0.4 Hz to maximum frequency, respectively.

Finally, the WBI function is determined. The goal of the WBI is to encourage healthy behaviors among individuals. Thus, exertion as well as meditation and relaxation are awarded a high index value. On the contrary, stressful situations that limit the HRV are given a low score. The WBI can be determined using the following equation:

WBI=$f_1$(HF/LF)+$f_2$(TP)+$f_3$(meanHR,HRmax)

where meanHR is the mean heart rate in bpm during the five minute window of interest, and HRmax is the maximum heart rate of the subject. In some embodiments, the Haskell and Fox formula, or any other suitable formula can be used to determine the HRmax.

The WBI provides a daily comprehensive value that indicates the quality of the day of the user from an HRV point of view. For example, a healthy nutritional regime increases the quality of sleep and wakefulness, and in turn the magnitude of HRV can urge the user towards such healthy behavior. Thus an increase of the daily WBI through weeks, months and years would indicate the effectiveness of the method described herein.

In this manner, the method described herein can allow the tracking of the level of the psychophysical health over a period of time. Awareness of a user's own well being level can provide the user encouragement as well as guidance to enhance daily interactions and quality of life. Furthermore, the method described herein can be incorporated in devices, for example, the wearable device 300 to help the user cope with stressful situations by providing compensational feedback, other than supporting healthy behaviors such as, for example, healthy eating and exercise.

While various embodiments of the system, methods and devices have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combination of components, other embodiments are possible having any combination or sub-combination of any features and/or components from any of the embodiments described herein. In addition, the specific configurations of the various components can also be varied. For example, the size and specific shape of the various components can be different than the embodiments shown, while still providing the functions as described herein.

The invention claimed is:

1. An apparatus, comprising:
a first electrode configured to be in contact with a first portion of a stratum corneum of skin;
a second electrode configured to be in contact with a second portion of the stratum corneum and in electronic communication with the first electrode through the stratum corneum;
a digital-to-analog converter (DAC) configured to generate a compensation voltage; and
a processor electrically coupled to the first electrode, the second electrode, and the DAC, the processor configured to execute computer-executable instructions to:
(a) bias the first electrode at a first voltage V+ and the second electrode at a second voltage V−;
(b) measure a first current flowing between the first electrode and the second electrode, the first current corresponding to a conductance of the stratum corneum;
(c) subtract a compensation current from the first current to obtain a second current;
(d) amplify the second current and transform the second current to an output voltage;
(e) calculate the conductance of the stratum corneum based on the output voltage, the conductance of the stratum corneum being indicative of an extent of electrodermal activity;
(f) determine whether the output voltage is greater than a threshold value; and
(g) in response to determining that the output voltage is greater than the threshold value, adjust the compensation voltage generated by the DAC to adjust the compensation current subtracted from the first current to prevent saturation of the output voltage.

2. The apparatus of claim 1, wherein the processor is further configured to execute computer-executable instructions to adjust the compensation voltage to decrease the compensation current if the output voltage falls below a predetermined minimum value.

3. The apparatus of claim 1, wherein the output voltage is indicative of a phasic value of the electrodermal activity.

4. The apparatus of claim 1, wherein the processor is further configured to execute computer-executable instructions to reverse a polarity of at least one of the first electrode and the second electrode after a predetermined period of time to reduce electrolysis.

5. The apparatus of claim 1, wherein the stratum corneum is a stratum corneum of any portion of a person's skin.

6. The apparatus of claim 5, wherein the conductance of the stratum corneum is a phasic level conductance, the processor further configured to execute the computer-executable instructions to calculate a tonic level conductance of the stratum corneum in the range of 0.05 μS to 50 μS.

7. The apparatus of claim 1, wherein the processor is configured to execute the computer-executable instructions to calculate the conductance of the stratum corneum with a resolution of 0.0001 μS.

8. The apparatus of claim 1, further comprising a wrist band including a housing, the processor is disposed in the housing.

9. The apparatus of claim 1, wherein the apparatus is at least one of a head band, an arm band, a foot band, an ankle band, or a ring.

10. The apparatus of claim 1, further comprising a heart beat sensor.

11. The apparatus of claim 10, further comprising at least one of an accelerometer, a temperature sensor, a blood oxygen sensor, and a glucose sensor.

12. The apparatus of claim 11, further comprising a communications module configured to communicate at least one of heart beat data, an accelerometer data, a temperature data, a blood oxygen data, and a glucose data to an external device.

13. The apparatus of claim 12, where the communication module is configured to communicate with the external device via at least one of a USB, USB 2.0, IEEE 1394, BLUETOOTH®, low powered BLUETOOTH®, and Wi-Fi.

14. The apparatus of claim 1, wherein the compensation current is a quasilinear function of the compensation voltage.

15. A method, comprising:
biasing a first electrode at a first voltage V+, the first electrode configured to be in contact with a first portion of a stratum corneum of a user;
biasing a second electrode at a second voltage V−, the second electrode configured to be in contact with a second portion of the stratum corneum and in electronic communication with the first electrode through the stratum corneum;
measuring a first current flowing between the first electrode and the second electrode, the first current corresponding to a conductance of the stratum corneum;
subtracting a compensation current from the first current to obtain a second current;
amplifying the second current and transforming the second current to an output voltage;
calculating the conductance of the stratum corneum based on the output voltage, the conductance of the stratum corneum being indicative of an extent of electrodermal activity;
generating a compensation voltage using a digital-to-analog converter (DAC);
determining whether the output voltage is greater than a threshold value; and
in response to determining that the output voltage is greater than the threshold value, adjusting the compensation voltage generated by the DAC to adjust the compensation current subtracted from the first current to prevent saturation of the output voltage.

16. The method of claim 15, further comprising reversing a polarity of at least one of the first electrode and the second electrode after a predetermined period of time to reduce electrolysis.

17. The method of claim 15, wherein the output voltage is indicative of a phasic value of the electrodermal activity.

18. The method of claim 15, further comprising adjusting the compensation voltage if the output voltage falls below a predetermined minimum value.

19. The method of claim 15, further comprising generating the compensation current as a quasilinear function of the compensation voltage.

* * * * *